(12) United States Patent
Hashimshony et al.

(10) Patent No.: US 8,116,845 B2
(45) Date of Patent: Feb. 14, 2012

(54) TISSUE-CHARACTERIZATION PROBE WITH EFFECTIVE SENSOR-TO-TISSUE CONTACT

(75) Inventors: Dan Hashimshony, Givat Ada (IL); Gil Cohen, Jerusalem (IL); Iddo Geltner, Herzlia (IL)

(73) Assignee: Dune Medical Devices Ltd., Caesaria (IL)

( * ) Notice: Subject to any disclaimer, the term of this patent is extended or adjusted under 35 U.S.C. 154(b) by 1469 days.

(21) Appl. No.: 11/350,102

(22) Filed: Feb. 9, 2006

(65) Prior Publication Data

US 2007/0032747 A1    Feb. 8, 2007

Related U.S. Application Data

(63) Continuation-in-part of application No. 11/196,732, filed on Aug. 4, 2005.

(51) Int. Cl.
*A61B 5/05* (2006.01)
*A61B 8/14* (2006.01)
*A61B 6/00* (2006.01)

(52) U.S. Cl. ......... 600/421; 600/415; 600/459; 600/474
(58) Field of Classification Search .................. 600/363, 600/407, 587, 301, 344, 386, 387, 415, 421, 600/459, 474
See application file for complete search history.

(56) References Cited

U.S. PATENT DOCUMENTS

| | | |
|---|---|---|
| 3,830,224 A | 8/1974 | Vanzetti et al. |
| RE30,317 E | 7/1980 | Lubbers et al. |
| 4,291,708 A | 9/1981 | Frei et al. |
| 4,344,440 A | 8/1982 | Aaby et al. |
| 4,458,694 A | 7/1984 | Sollish et al. |
| 4,537,203 A | 8/1985 | Machida |
| 4,539,640 A | 9/1985 | Fry et al. |
| RE32,000 E | 10/1985 | Sagi |
| 4,617,939 A | 10/1986 | Brown et al. |
| 4,625,171 A | 11/1986 | Sekihara et al. |
| 4,682,594 A | 7/1987 | Mok |
| 4,689,567 A | 8/1987 | Maudsley |

(Continued)

FOREIGN PATENT DOCUMENTS

DE    19705260 A1    8/1997

(Continued)

OTHER PUBLICATIONS

Schwan "Mechanism Responsible for Electrical Properties of Tissues and Cell Suspensions", Medical Process Through Technology, 19: 163-165, 1993.

(Continued)

*Primary Examiner* — Max Hindenburg
*Assistant Examiner* — Emily Lloyd

(57) ABSTRACT

The present invention relates to a device for tissue-characterization, designed for effective sensor-to-tissue contact. The device includes an element, having a rigid surface of a linear cross-section, on which at least one sensor is arranged, and a mechanism for applying a force to a soft tissue, the line of force being at an acute angle with the rigid surface, for stretching or stretching and pushing the soft tissue against the rigid surface, thus achieving effective contact between the tissue and the at least one sensor. In consequence, the accuracy of the sensing is improved. In accordance with another embodiment, a plurality of sensors is employed, arranged along a curved element, for providing three-dimensional information regarding the tissue, for example, by small-scale computerized tomography.

45 Claims, 23 Drawing Sheets

U.S. PATENT DOCUMENTS

| | | |
|---|---|---|
| 4,751,464 A | 6/1988 | Bridges |
| 4,768,513 A | 9/1988 | Suzuki |
| 4,779,624 A | 10/1988 | Yokoi |
| 4,785,806 A | 11/1988 | Deckelbaum |
| 5,115,137 A | 5/1992 | Andersson-Engels et al. |
| 5,143,079 A | 9/1992 | Frei et al. |
| 5,227,730 A | 7/1993 | King et al. |
| 5,277,730 A | 1/1994 | Darsey et al. |
| 5,334,941 A | 8/1994 | King |
| 5,383,454 A | 1/1995 | Bucholz |
| 5,442,290 A | 8/1995 | Crooks |
| 5,482,041 A | 1/1996 | Wilk et al. |
| 5,482,047 A | 1/1996 | Nordgren et al. |
| 5,558,092 A | 9/1996 | Unger et al. |
| 5,572,132 A | 11/1996 | Pulyer et al. |
| 5,630,426 A | 5/1997 | Eggers et al. |
| 5,678,565 A | 10/1997 | Sarvazyan |
| 5,699,804 A | 12/1997 | Rattner |
| 5,704,355 A | 1/1998 | Bridges |
| 5,727,569 A | 3/1998 | Benetti et al. |
| 5,735,278 A | 4/1998 | Hoult et al. |
| 5,744,971 A | 4/1998 | Chan et al. |
| 5,758,646 A | 6/1998 | Van Der Meulen et al. |
| 5,800,350 A | 9/1998 | Coppelson et al. |
| 5,807,257 A | 9/1998 | Bridges |
| 5,810,742 A | 9/1998 | Pearlman |
| 5,821,410 A | 10/1998 | Xiang et al. |
| 5,829,437 A | 11/1998 | Bridges et al. |
| 5,830,145 A | 11/1998 | Tenhoff |
| 5,884,239 A | 3/1999 | Romanik, Jr. |
| 5,900,618 A | 5/1999 | Anlage et al. |
| 5,927,284 A | 7/1999 | Borst et al. |
| 6,004,263 A | 12/1999 | Nakaichi et al. |
| 6,010,455 A | 1/2000 | Barnett et al. |
| 6,026,323 A | 2/2000 | Skladnev et al. |
| 6,055,451 A | 4/2000 | Bambot et al. |
| 6,055,452 A | 4/2000 | Pearlman |
| 6,061,589 A | 5/2000 | Bridges et al. |
| 6,064,081 A | 5/2000 | Robinson et al. |
| 6,071,239 A | 6/2000 | Cribbs et al. |
| 6,081,738 A | 6/2000 | Hinohara et al. |
| 6,086,534 A | 7/2000 | Kesten |
| 6,090,041 A | 7/2000 | Clark et al. |
| 6,093,150 A | 7/2000 | Chandler et al. |
| 6,109,270 A | 8/2000 | Mah et al. |
| 6,135,968 A | 10/2000 | Brounstein |
| 6,167,297 A | 12/2000 | Benaron |
| 6,173,604 B1 | 1/2001 | Xiang et al. |
| 6,203,533 B1 | 3/2001 | Ouchi |
| 6,233,479 B1 | 5/2001 | Haddad et al. |
| 6,258,576 B1 | 7/2001 | Richards-Kortum et al. |
| 6,280,704 B1 | 8/2001 | Schutt et al. |
| 6,287,302 B1 | 9/2001 | Berube |
| 6,308,097 B1 | 10/2001 | Pearlman |
| 6,315,981 B1 | 11/2001 | Unger |
| 6,321,106 B1 | 11/2001 | Lemelson |
| 6,331,166 B1 | 12/2001 | Burbank et al. |
| 6,370,426 B1 | 4/2002 | Campbell et al. |
| 6,375,634 B1 | 4/2002 | Carroll |
| 6,377,841 B1 | 4/2002 | Lin et al. |
| 6,380,747 B1 | 4/2002 | Goldfine et al. |
| 6,397,095 B1 | 5/2002 | Eyuboglu et al. |
| 6,405,733 B1 | 6/2002 | Fogarty et al. |
| 6,411,103 B1 | 6/2002 | Tobais et al. |
| 6,500,112 B1 | 12/2002 | Khouri |
| 6,530,944 B2 | 3/2003 | West et al. |
| 6,544,185 B2 | 4/2003 | Montegrande |
| 6,546,787 B1 | 4/2003 | Schiller et al. |
| 6,564,806 B1 | 5/2003 | Fogarty et al. |
| 6,592,520 B1 | 7/2003 | Peszynski et al. |
| 6,597,185 B1 | 7/2003 | Talanov et al. |
| 6,671,540 B1 | 12/2003 | Hochman |
| 6,677,755 B2 | 1/2004 | Belt et al. |
| 6,695,782 B2 | 2/2004 | Ranucci et al. |
| 6,699,206 B2 | 3/2004 | Burbank et al. |
| 6,722,371 B1 | 4/2004 | Bush et al. |
| 6,728,565 B2 | 4/2004 | Wendlandt |
| 6,741,077 B2 | 5/2004 | Yokoyama et al. |
| 6,747,454 B2 | 6/2004 | Belt |
| 6,752,154 B2 | 6/2004 | Fogarty et al. |
| 6,766,185 B2 | 7/2004 | Scott |
| 6,813,515 B2 | 11/2004 | Hashimshony |
| 6,840,948 B2 | 1/2005 | Albrecht et al. |
| 6,909,084 B2 | 6/2005 | Tachi et al. |
| 6,936,003 B2 | 8/2005 | Iddan |
| 6,962,587 B2 | 11/2005 | Johnson et al. |
| 7,082,325 B2 | 7/2006 | Hashimshony et al. |
| 7,184,824 B2 | 2/2007 | Hashimshony |
| 2001/0051774 A1 | 12/2001 | Littrup et al. |
| 2002/0055754 A1 | 5/2002 | Ranucci et al. |
| 2002/0059938 A1 | 5/2002 | Fogarty et al. |
| 2002/0068880 A1 | 6/2002 | Burbank et al. |
| 2002/0072676 A1* | 6/2002 | Afanassieva ............... 600/473 |
| 2002/0120265 A1 | 8/2002 | Fowler |
| 2002/0148277 A1 | 10/2002 | Umeda |
| 2003/0036674 A1 | 2/2003 | Bouton |
| 2003/0045798 A1 | 3/2003 | Hular et al. |
| 2003/0062897 A1 | 4/2003 | Belt et al. |
| 2003/0117140 A1 | 6/2003 | Belt et al. |
| 2003/0138378 A1 | 7/2003 | Hashimshony |
| 2003/0146814 A1 | 8/2003 | Wiltshire |
| 2003/0163037 A1 | 8/2003 | Bladen et al. |
| 2003/0171664 A1 | 9/2003 | Wendlandt |
| 2003/0187347 A1 | 10/2003 | Nevo et al. |
| 2003/0187366 A1 | 10/2003 | Hashimshony |
| 2003/0199753 A1 | 10/2003 | Hibner et al. |
| 2003/0216648 A1 | 11/2003 | Lizzi et al. |
| 2003/0229343 A1 | 12/2003 | Albrecht et al. |
| 2004/0065158 A1 | 4/2004 | Schrepfer et al. |
| 2004/0168692 A1 | 9/2004 | Fogarty et al. |
| 2004/0254457 A1 | 12/2004 | Van der Weide |
| 2005/0010131 A1 | 1/2005 | Burbank et al. |
| 2005/0021019 A1 | 1/2005 | Hashimshony et al. |
| 2005/0107717 A1 | 5/2005 | Yamamoto et al. |
| 2005/0119648 A1 | 6/2005 | Swanson |
| 2005/0159689 A1 | 7/2005 | Olson |
| 2006/0253107 A1 | 11/2006 | Hashimshony et al. |
| 2006/0264738 A1 | 11/2006 | Hashimshony et al. |
| 2007/0032739 A1 | 2/2007 | Hashimshony et al. |
| 2007/0032747 A1 | 2/2007 | Hashimshony et al. |
| 2007/0092059 A1* | 4/2007 | Wayne Eberhard et al. .. 600/437 |
| 2007/0179397 A1 | 8/2007 | Hashimshony et al. |
| 2007/0255169 A1 | 11/2007 | Hashimshony et al. |
| 2007/0260156 A1 | 11/2007 | Hashimshony |
| 2008/0021343 A1 | 1/2008 | Hashimshony et al. |
| 2008/0039742 A1 | 2/2008 | Hashimshony et al. |
| 2008/0154090 A1 | 6/2008 | Hashimshony |
| 2008/0287750 A1 | 11/2008 | Hashimshony et al. |
| 2009/0062637 A1 | 3/2009 | Hashimshony et al. |

FOREIGN PATENT DOCUMENTS

| | | |
|---|---|---|
| DE | 19734978 A1 | 2/1999 |
| EP | 419235 | 3/1991 |
| GB | 01153980 | 3/1968 |
| JP | 05-018924 | 1/1993 |
| JP | 05-068666 | 3/1993 |
| JP | 06-296578 | 10/1994 |
| JP | 09-243576 | 9/1997 |
| JP | 2004-016556 | 1/2004 |
| WO | WO 97/12553 | 4/1997 |
| WO | WO 01/42807 | 6/2001 |
| WO | WO 01/43630 | 6/2001 |
| WO | WO 01/65240 | 7/2001 |
| WO | WO 01/65240 | 9/2001 |
| WO | WO 02/32335 | 4/2002 |
| WO | WO 02/058531 | 8/2002 |
| WO | WO 03/009752 | 2/2003 |
| WO | WO 03/060462 | 7/2003 |
| WO | WO 2005/009200 | 2/2005 |
| WO | WO 2005/089065 | 9/2005 |
| WO | WO 2006/072947 | 7/2006 |
| WO | WO 2006/092797 | 9/2006 |
| WO | WO 2006/103665 | 10/2006 |
| WO | WO 2007/015255 | 2/2007 |
| WO | WO 2007/083310 | 7/2007 |
| WO | WO 2008/132714 | 11/2008 |
| WO | WO 2008/132750 | 11/2008 |

OTHER PUBLICATIONS

Smith et al. "In Vivo Measurement of Tumor Conductiveness With the Magnetic Bioimpedance Method", IEEE Transactions on Biomedical Engineering, 47(10): 1403-1405, 2000.
Surowiec et al. "Dielectric Properties of Breast Carcinoma and the Surrounding Tissues", IEEE Transactions on Biomedical Engineering, 35(4): 257-263, 1988.
Official Action Dated Sep. 29, 2010 From the US Patent and Trademark Office Re.: U.S. Appl. No. 11/797,167.
Translation of Notice of Reason for Rejection Dated Aug. 24, 2010 From the Japanese Patent Office Re. Application No. 2006-520980.
Official Action Dated Jul. 9, 2010 From the US Patent and Trademark Office Re.: U.S. Appl. No. 11/705,143.
Rajshekhar "Continuous Impedence Monitoring During CT-Guided Stereotactic Surgery: Relative Value in Cystic and Solid Lesions", British Journal of Neurosurgery, 6: 439-444, 1992.
Brown "A Survey of Image Registration Techniques", ACM Computing Surveys, 24(4): 325-376, 1992.
Notice of Allowance Dated Jun. 29, 2010 From the US Patent and Trademark Office Re.: U.S. Appl. No. 11/487,431.
Response Dated Aug. 4, 2010 to Official Action of Feb. 4, 2010 From the US Patent and Trademark Office Re.: U.S. Appl. No. 11/196,732.
Notification to Grant Patent Right for Invention Dated Aug. 3, 2010 From the State Intellectual Property Office of the People's Republic of China Re.: Application No. 200680019026.4 and Its Translation Into English.
Communication Pursuant to Article 94(3) EPC Dated Oct. 7, 2009 From the European Patent Office Re.: Application No. 06728196.4.
International Preliminary Report on Patentability Dated Nov. 12, 2009 From the International Bureau of WIPO Re.: Application No. PCT/IL2008/000406.
Official Action Dated Aug. 27, 2009 From the US Patent and Trademark Office Re.: U.S. Appl. No. 11/705,143.
Official Action Dated Aug. 27, 2009 From the US Patent and Trademark Office Re.: U.S. Appl. No. 11/797,167.
Official Action Dated Oct. 27, 2009 From the US Patent and Trademark Office Re.: U.S. Appl. No. 11/487,431.
Official Action Dated Aug. 31, 2009 From the US Patent and Trademark Office Re.: U.S. Appl. No. 11/797,166.
Response Dated Oct. 13, 2009 to Official Action of Sep. 15, 2009 From the US Patent and Trademark Office Re.: U.S. Appl. No. 11/196,732.
Response Dated Oct. 13, 2009 to Official Action of Dec. 18, 2008 From the US Patent and Trademark Office Re.: U.S. Appl. No. 10/534,544.
Response Dated Nov. 25, 2009 to Official Action of Aug. 27, 2009 From the US Patent and Trademark Office Re.: U.S. Appl. No. 11/705,143.
Response Dated Nov. 25, 2009 to Official Action of Aug. 27, 2009 From the US Patent and Trademark Office Re.: U.S. Appl. No. 11/797,167.
Supplementary Partial European Search Report and the European Searching Opinion Dated Dec. 4, 2009 From the European Patent Office Re.: Application No. 06700052.1.
Translation of Office Action Dated Sep. 18, 2009 From the State Intellectual Property Office of the People's Republic of China Re.: Application No. 200680006513.7.
Response Dated Sep. 2, 2010 to Communication Pursuant to Article 94(3) EPC of Mar. 15, 2010 From the European Patent Office Re.: Application No. 06700052.1.
Response Dated Aug. 30, 2010 to Official Action of Mar. 11, 2010 From the US Patent and Trademark Office Re.: U.S. Appl. No. 11/797,166.
Translation of Notification to Grant Patent Right for Invention Dated Aug. 3, 2010 From the State Intellectual Property Office of the People's Republic of China Re.: Application No. 200680019026.4.
Examination Report Dated Feb. 1, 2008 From the Government of India, Patent Office Re.: Application No. 668/CHENP/2006.
International Preliminary Report on Patentability Dated Jan. 22, 2009 From the International Bureau of WIPO Re.: Application No. PCT/IL2006/000908.
International Preliminary Report on Patentatbility Dated Aug. 9, 2007 From the International Bureau of WIPO Re.: Applicaiton No. PCT/IL2006/000015.
International Search Report and the Written Opinion Dated May 3, 2007 From the International Searching Authority Re.: Application No. PCT/IL06/00392.
International Search Report and the Written Opinion Dated Feb. 5, 2007 From the International Searching Authority Re.: Application No. PCT/IL05/00330.
International Search Report and the Written Opinion Dated Jun. 22, 2005 From the International Searching Authority Re.: Application No. PCT/IL04/00641.
Supplementary European Search Report Dated Feb. 17, 2005 From the European Patent Office Re.: Application No. 02795418.9.
Misra et al. "Noninvasive Electrical Characterization of Materials at Microwave Frequencies Using An Open-Ended Coaxial Line: Test of An Improved Calibration Technique", IEEE Transactions on Microwave Theory & Techniques, 38(1): 8-13, 1990.
Burdette et al. "In Vivo Probe Measurement Technique for Determining Dielectric Properties at VFW Through Microwave Frequencies", IEEE Transactions on Microwave Theory & Techniques, MTT-28(4): 414-427, 1980.
Xu et al. "Measurement of Microwave Permittivity Using Open Ended Elliptical Coaxial Probes", IEEE Transactions on Microwave Theory & Techniques, 40(1): 143-150, 1992.
Stuchly et al. "Measurement of Radio Frequency Permittivity of Biological Tissues With An Open-Ended Coaxial Line: Part II-Experimental Results", IEEE Transactions on Microwave Theory & Techniques, MTT-30(1): 87-91, 1982.
Mosig et al. "Reflection of An Open-Ended Coaxial Line", IEEE Transactions on Instrumentation & Measurement, IM-30(1): 46-51, 1981.
Supplementary European Search Report and the European Search Opinion Dated Jun. 5, 2009 From the European Patent Office Re.: Application No. 06728196.4.
Communication Pursuant to Article 96(2) EPC Dated Aug. 10, 2006 From the European Patent Office Re.: Application No. 02795418.9.
Communication Pursuant to Article 96(2) EPC Dated Jan. 12, 2006 From the European Patent Office Re.: Application No. 02795418.9.
Communication Relating to the Results of the Partial International Search Dated Sep. 1, 2008 From the International Searching Authority Re.: Application No. PCT/IL2008/000406.
International Preliminary Report on Patentability Dated Feb. 4, 2008 From the International Preliminary Examining Authority Re.: Application No. PCT/IL06/00392.
International Preliminary Report on Patentability Dated Apr. 26, 2007 From the International Bureau of WIPO Re.: Application No. PCT/IL2005/000330.
International Preliminary Report on Patentability Dated Aug. 9, 2007 From the International Bureau of WIPO Re.: Application No. PCT/IL2006/000015.
Office Action Dated Feb. 11, 2009 From the Israeli Patent Office Re.: Application No. 173231 and Its Translation Into English.
Office Action Dated Nov. 18, 2008 From the Government of India, Patent Office Re.: Application No. 668/CHENP/2006.
Office Action Dated Mar. 20, 2009 From the State Intellectual Property Office of the People's Republic of China Re.: Application No. 200680019026.4.
Official Action Dated Apr. 1, 2008 From US Patent and Trademark Office Re.: U.S. Appl. No. 11/745,334.
Official Action Dated Jun. 3, 2005 From the US Patent and Trademark Office Re.: U.S. Appl. No. 10/891,750.
Official Action Dated Jun. 4, 2007 From the US Patent and Trademark Office Re.: U.S. Appl. No. 10/298,196.
Official Action Dated Jul. 9, 2008 From the US Patent and Trademark Office Re.: U.S. Appl. No. 11/196,732.
Official Action Dated Apr. 10, 2006 From the US Patent and Trademark Office Re.: U.S. Appl. No. 10/965,752.
Official Action Dated Feb. 10, 2006 From the US Patent and Trademark Office Re.: U.S. Appl. No. 10/298,196.
Official Action Dated Oct. 10, 2006 From the US Patent and Trademark Office Re.: U.S. Appl. No. 10/298,196.

Official Action Dated Nov. 19, 2007 From the US Patent and Trademark Office Re.: U.S. Appl. No. 11/196,732.
Official Action Dated Mar. 21, 2008 From the US Patent and Trademark Office Re.: U.S. Appl. No. 10/558,831.
Official Action Dated Jan. 24, 2008 From the US Patent and Trademark Office Re.: U.S. Appl. No. 10/298,196.
Response Dated Aug. 3, 2007 to Written Opinion of May 3, 2007 From the International Searching Authority Re.: Application No. PCT/IL06/00392.
Response Dated Jan. 4, 2007 to Communication Pursuant to Article 96(2) of Aug. 10, 2006 From the European Patent Office Re.: Application No. 02795418.9.
Response Dated Mar. 16, 2007 to Communication Pursuant to Article 96(2) EPC of Jan. 19, 2007 From the European Patent Office Re.: Application No. 02795418.9.
Communication Pursuant to Article 94(3) EPC Dated Mar. 15, 2010 From the European Patent Office Re.: Application No. 06700052.1.
Examination Report Dated Feb. 1, 2008 From the Goverment of India, Patent Office Re.: Application No. 668/CHENP/2006.
Examination Report Dated Nov. 18, 2008 From the Government of India, Patent Office Re.: Application No. 668/CHENP/2006.
International Search Report Dated Nov. 27, 2008 From the International Searching Authority Re.: Application No. PCT/IL2008/000406.
Notice of Allowance Dated Oct. 20, 2006 From the US Patent and Trademark Office Re.: U.S. Appl. No. 10/965,752.
Official Action Dated Feb. 4, 2010 From the US Patent and Trademark Office Re.: U.S. Appl. No. 11/196,732.
Official Action Dated Mar. 11, 2010 From the US Patent and Trademark Office Re.: U.S. Appl. No. 11/797,166.
Official Action Dated Mar. 16, 2010 From the US Patent and Trademark Office Re.: U.S. Appl. No. 11/887,571.
Official Action Dated Mar. 17, 1010 From the US Patent and Trademark Office Re.: U.S. Appl. No. 10/567,581.
Reponse Dated Mar. 1, 2010 to Official Action of Oct. 27, 2009 From the US Patent and Trademark Office Re.: U.S. Appl. No. 11/487,431.
Response Dated Jan. 3, 2010 to Office Action of Sep. 18, 2009 From the State Intellectual Property Office of the People's Republic of China Re.: Application No. 200680006513.7.
Response Dated Jan. 7, 2010 to Official Action of Dec. 7, 2009 From the US Patent and Trademark Office Re.: U.S. Appl. No. 11/797,167.
Response Dated Feb. 8, 2010 to Communication Pursuant to Article 94(3) EPC of Oct. 7, 2009 From the European Patent Office Re.: Application No. 06728196.4.
Response Dated Dec. 30, 2009 to Official Action of Aug. 31, 2009 From the US Patent and Trademark Office Re.: U.S. Appl. No. 11/797,166.
Translation of the Notice of Reason for Rejection Dated Oct. 31, 2008 From the Japanese Patent Office Re.: Application No. 2003-560509.
Translation of the Office Action Dated Jul. 27, 2007 From the Patent Office of the People's Republic of China Re.: Application No. 200480027097.X.
Written Opinion Dated Nov. 27, 2008 From the International Searching Authority Re.: Application No. PCT/IL2008/000406.
Response Dated Sep. 16, 2010 to Official Action of Mar. 16, 2010 From the US Patent and Trademark Office Re.: U.S. Appl. No. 11/887,571.
Partial International Search Dated Sep. 1, 2008 From the International Searching Authority Re.: Application No. PCT/IL2008/000406.
Communication Pursuant to Article 94(3) EPC Dated Sep. 27, 2010 From the European Patent Office Re.: Application No. 06728196.4.
Response Dated Sep. 16, 2010 to Official Action of Mar. 17, 1010 From the US Patent and Trademark Office Re.: U.S. Appl. No. 10/567,581.
Official Action Dated Dec. 8, 2010 From the US Patent and Trademark Office Re.: U.S. Appl. No. 11/196,732.
Official Action Dated Nov. 23, 2010 From the US Patent and Trademark Office Re.: U.S. Appl. No. 10/567,581.
Response Dated Jun. 6, 2011 to Official Action Dated Dec. 8, 2010 From the US Patent and Trademark Office Re.: U.S. Appl. No. 11/196,732.
Response Dated May 23, 2011 to Official Action of Nov. 23, 2010 From the US Patent and Trademark Office Re.: U.S. Appl. No. 10/567,581.
Translation of Notice of Reason for Rejection Dated Feb. 15, 2011 From the Japanese Patent Office Re. Application No. 2006-520980.
Notice of Allowance Dated Jun. 10, 2011 From the US Patent and Trademark Office Re.: U.S. Appl. No. 11/797,167.
Response Dated May 30, 2011 to Communication Pursuant to Article 94(3) EPC of Feb. 1, 2011 From the European Patent Office Re.: Application No. 06700052.1.
Official Action Dated Aug. 18, 2011 From the US Patent and Trademark Office Re. U.S. Appl. No. 11/196,732.
Translation of Notice of Reason for Rejection Dated Aug. 19, 2011 From the Japanese Patent Office Re. Application No. 2007-550012.
Response Dated Apr. 28, 2011 to Official Action of Oct. 28, 2010 From the US Patent and Trademark Office Re.: U.S. Appl. No. 11/797,166.
Official Action Dated Jul. 8, 2011 From the US Patent and Trademark Office Re.: U.S. Appl. No. 11/797,166.
Translation of Office Action Dated Jun. 30, 2011 From the State Intellectual Property Office of the People's Republic of China Re.: Application No. 200680006513.7.
Translation of Notice of Reason for Rejection Dated Jul. 12, 2011 From the Japanese Patent Office Re. Application No. 2008-503679.
Response Dated Dec. 27, 2010 to Official Action of Jul. 9, 2010 From the US Patent and Trademark Office Re.: U.S. Appl. No. 11/705,143.
Communication Pursuant to Article 94(3) EPC Dated Feb. 1, 2011 From the European Patent Office Re.: Application No. 06700052.1.
Response Dated Jan. 26, 2011 to Office Action of Aug. 4, 2010 From the State Intellectual Property Office of the People's Republic of China Re. Application No. 200680037103.9.
Translation of Office Action Dated Aug. 4, 2010 From the State Intellectual Property Office of the People's Republic of China Re. Application No. 200680037103.9.
Response Dated Mar. 29, 2011 to Official Action of Sep. 29, 2010 From the US Patent and Trademark Office Re.: U.S. Appl. No. 11/797,167.
Notice of Allowance Dated May 17, 2011 From the US Patent and Trademark Office Re.: U.S. Appl. No. 11/705,143.
Official Action Dated Oct. 28, 2010 From the US Patent and Trademark Office Re.: U.S. Appl. No. 11/797,166.
Response Dated Mar. 28, 2011 to Communication Pursuant to Article 94(3) EPC of Sep. 27, 2010 From the European Patent Office Re.: Application No. 06728196.4.
Response Dated Jan. 16, 2011 to Notice of Reason for Rejection of Aug. 24, 2010 From the Japanese Patent Office Re. Application No. 2006-520980.
Translation of Notice of Reason for Rejection Dated Nov. 4, 2011 From the Japanese Patent Office Re. Application No. 2008-524676.

* cited by examiner

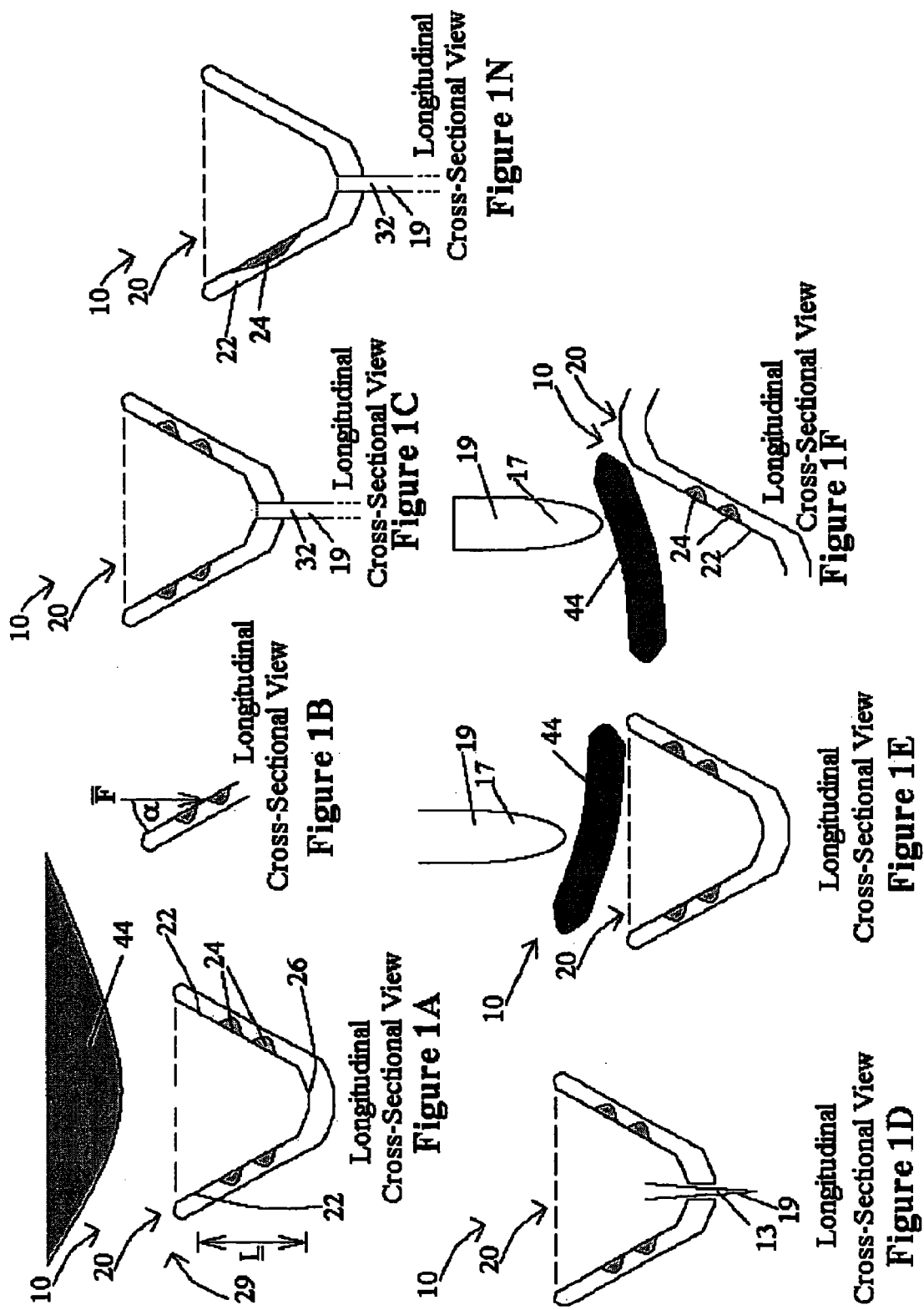

Cross-Sectional View

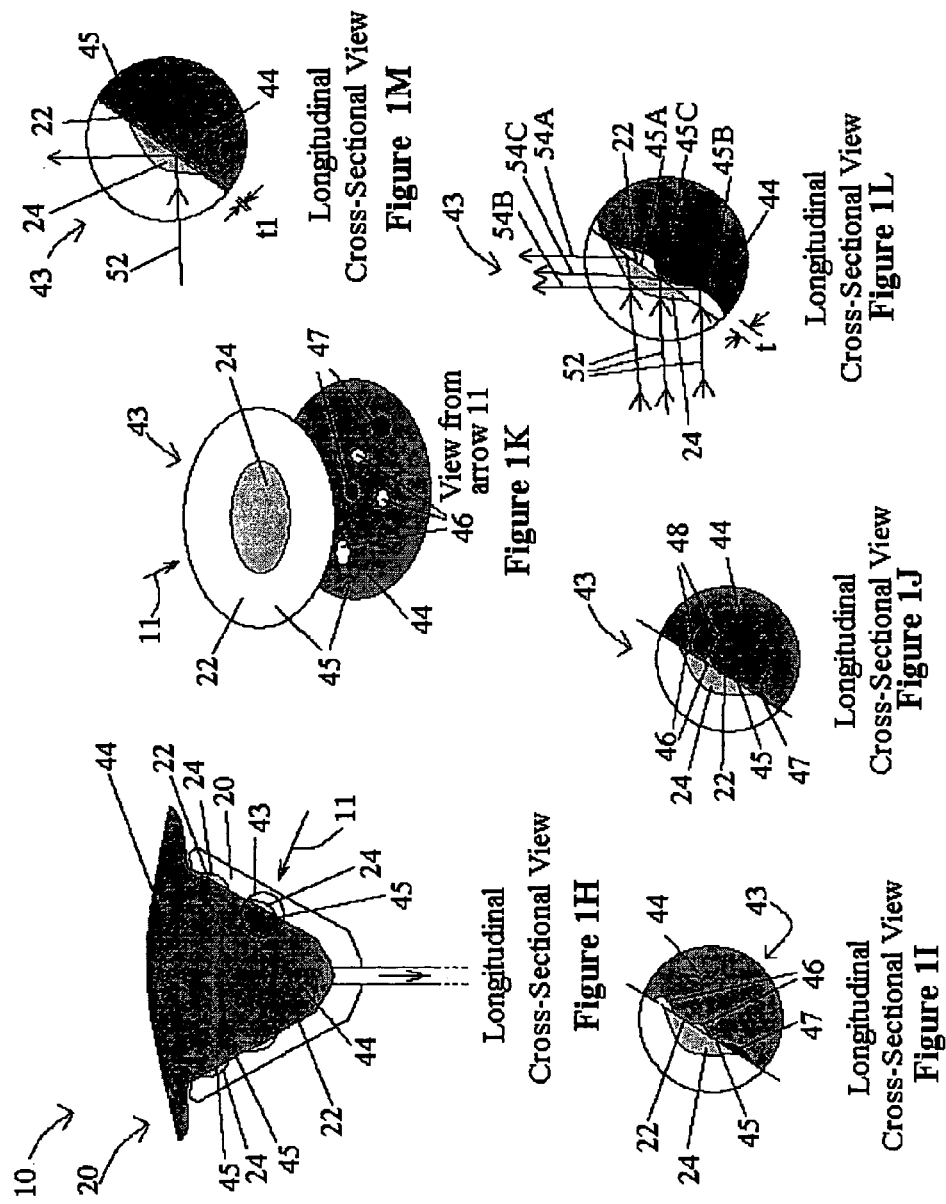

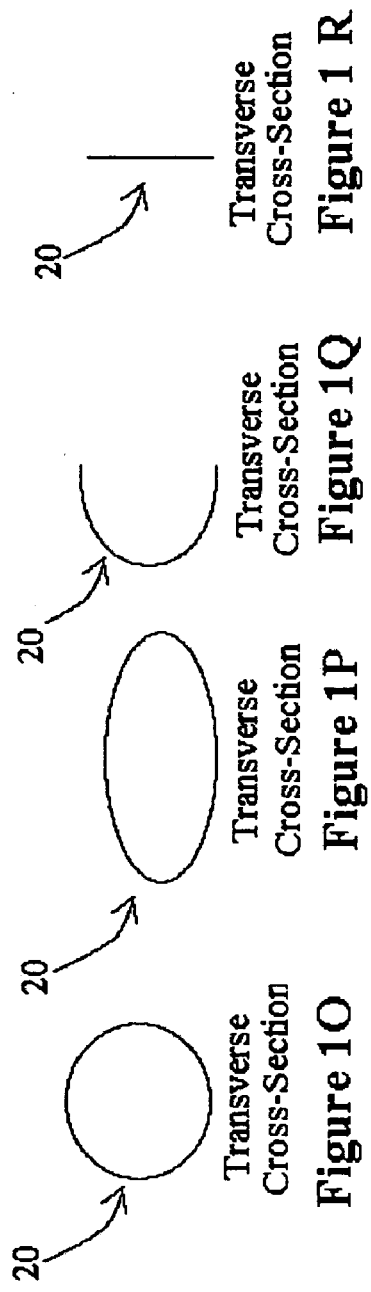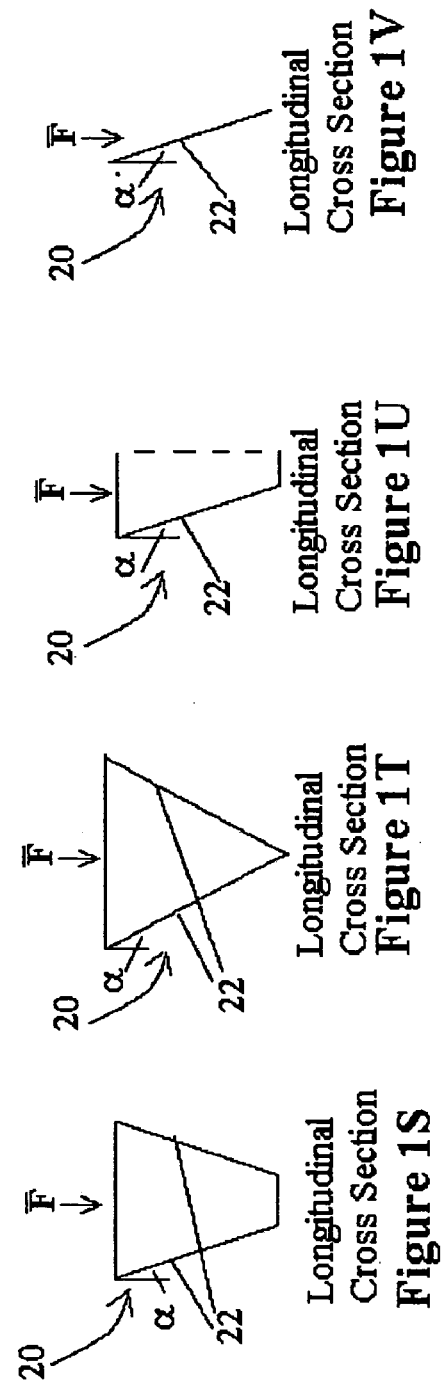

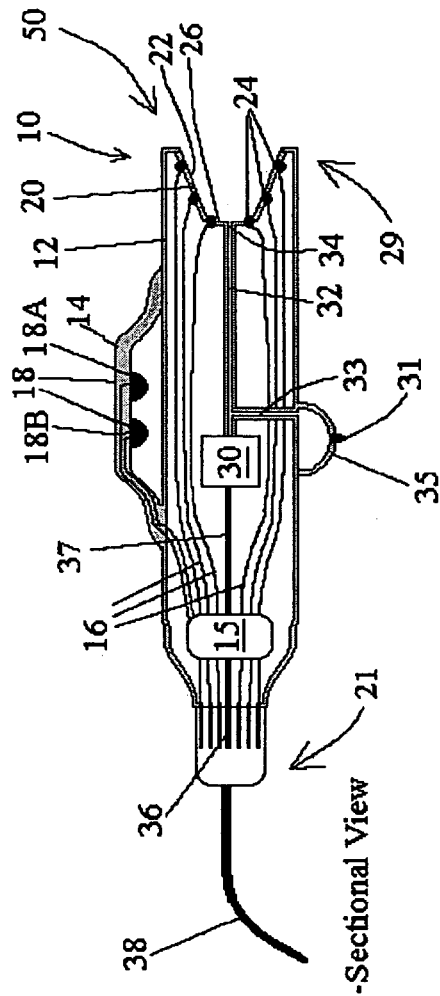
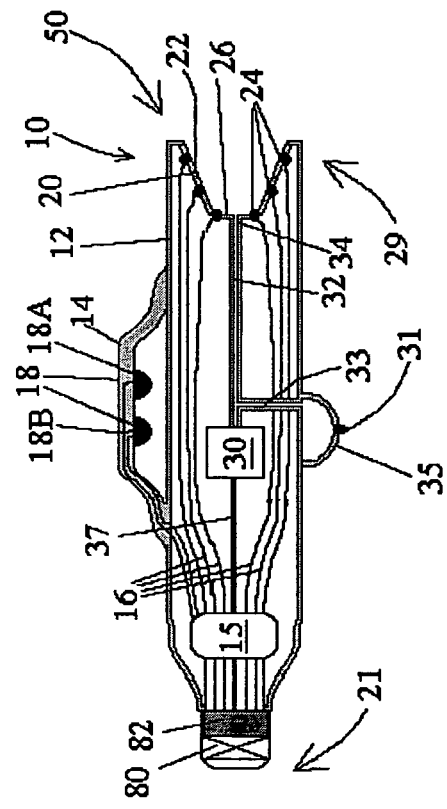
Longitudinal Cross-Sectional View
Figure 2A
Longitudinal Cross-Sectional View
Figure 2B

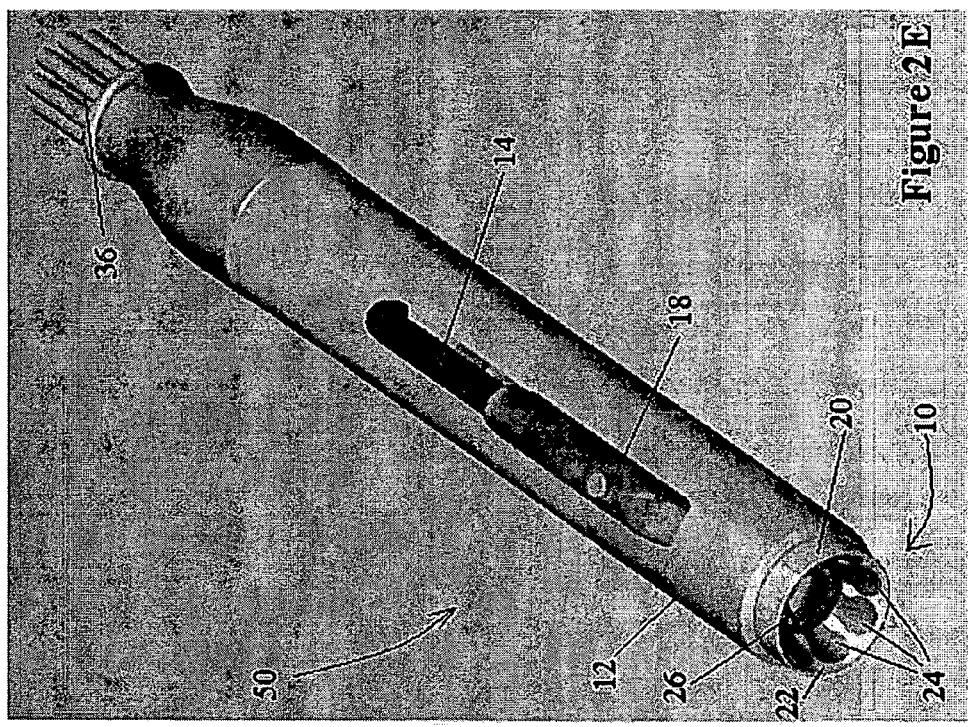

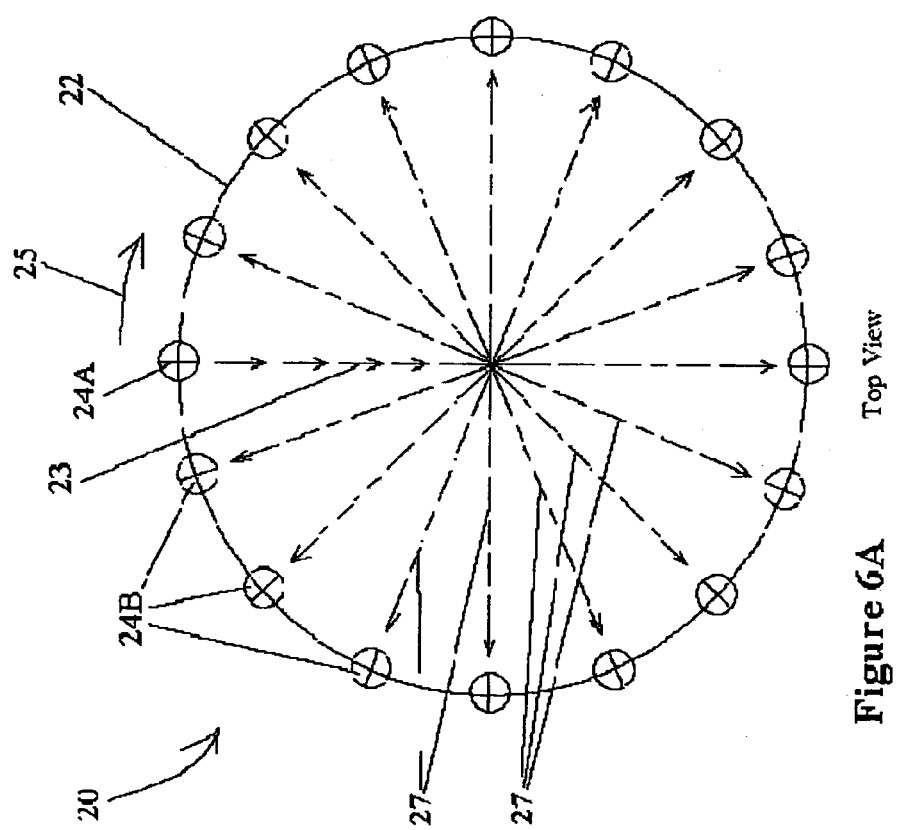

Side View

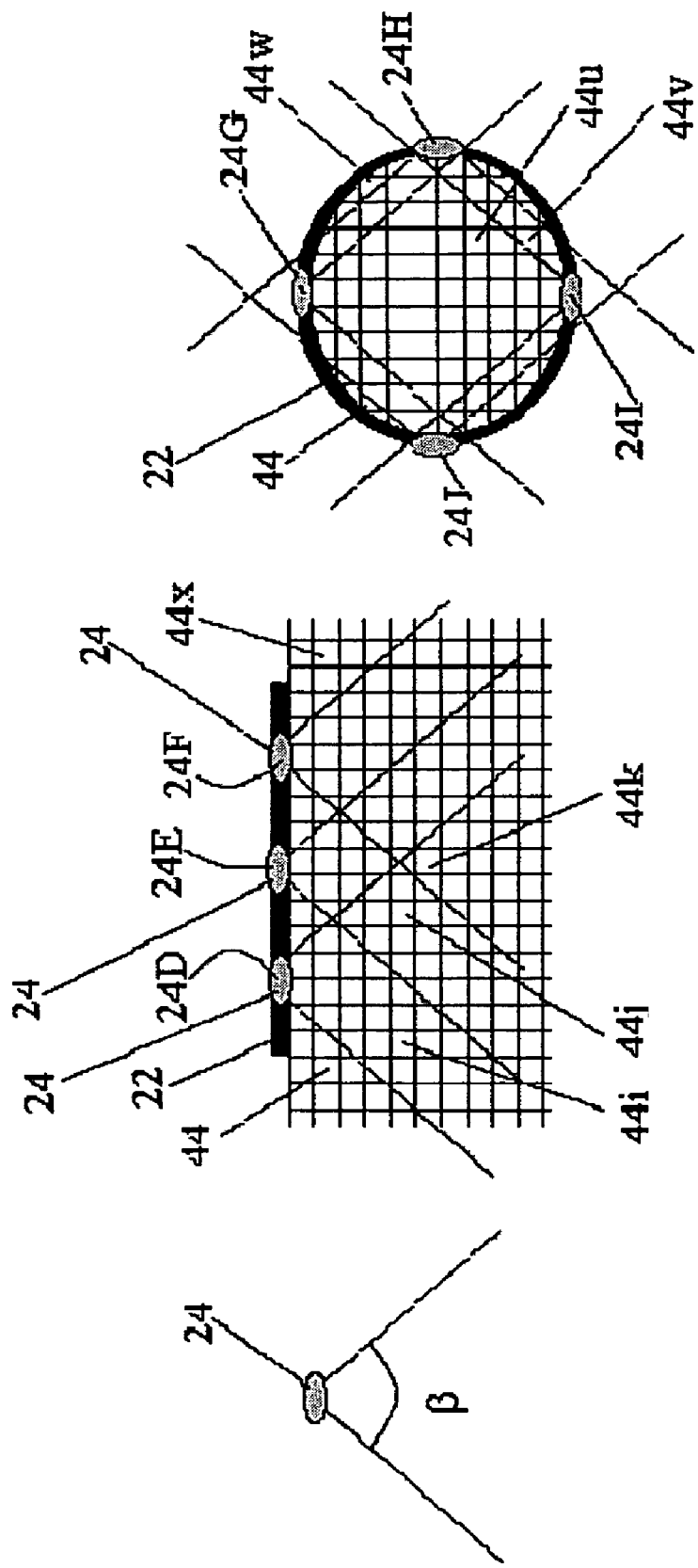

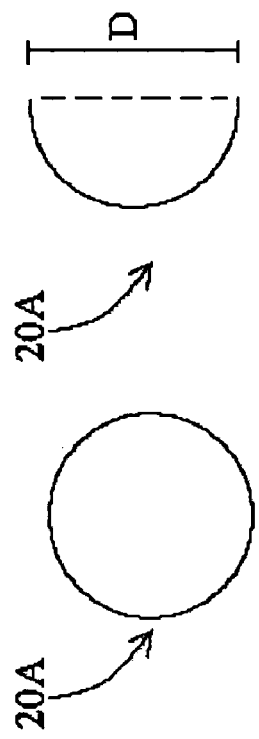
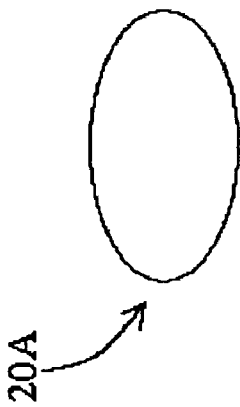
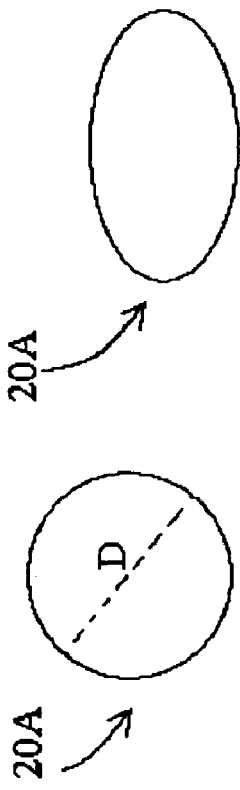
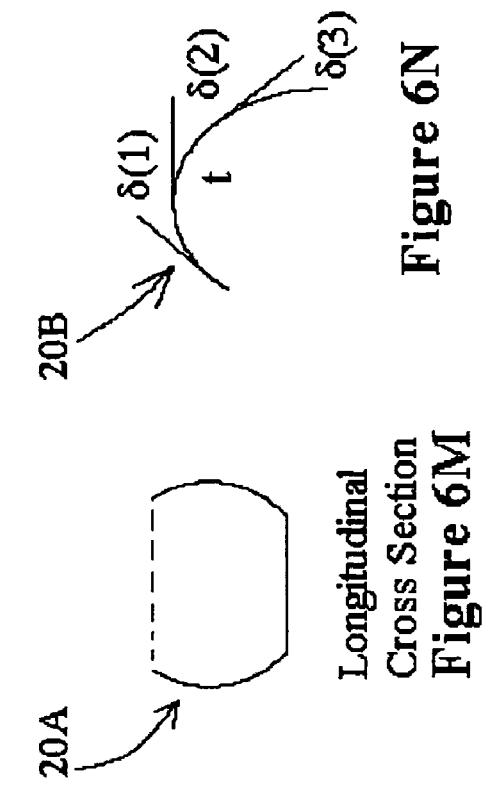
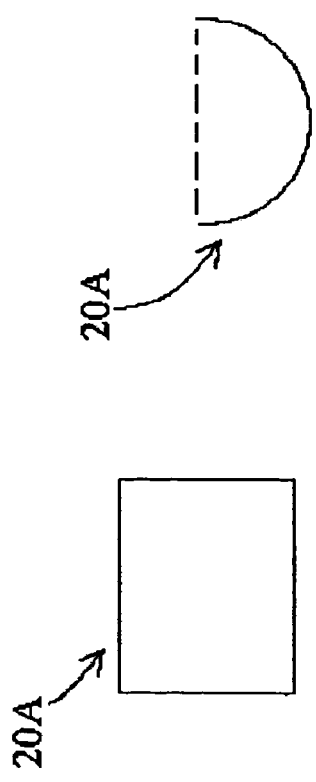
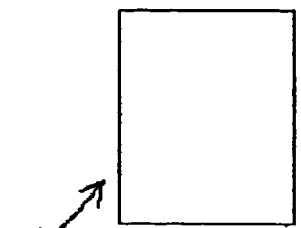

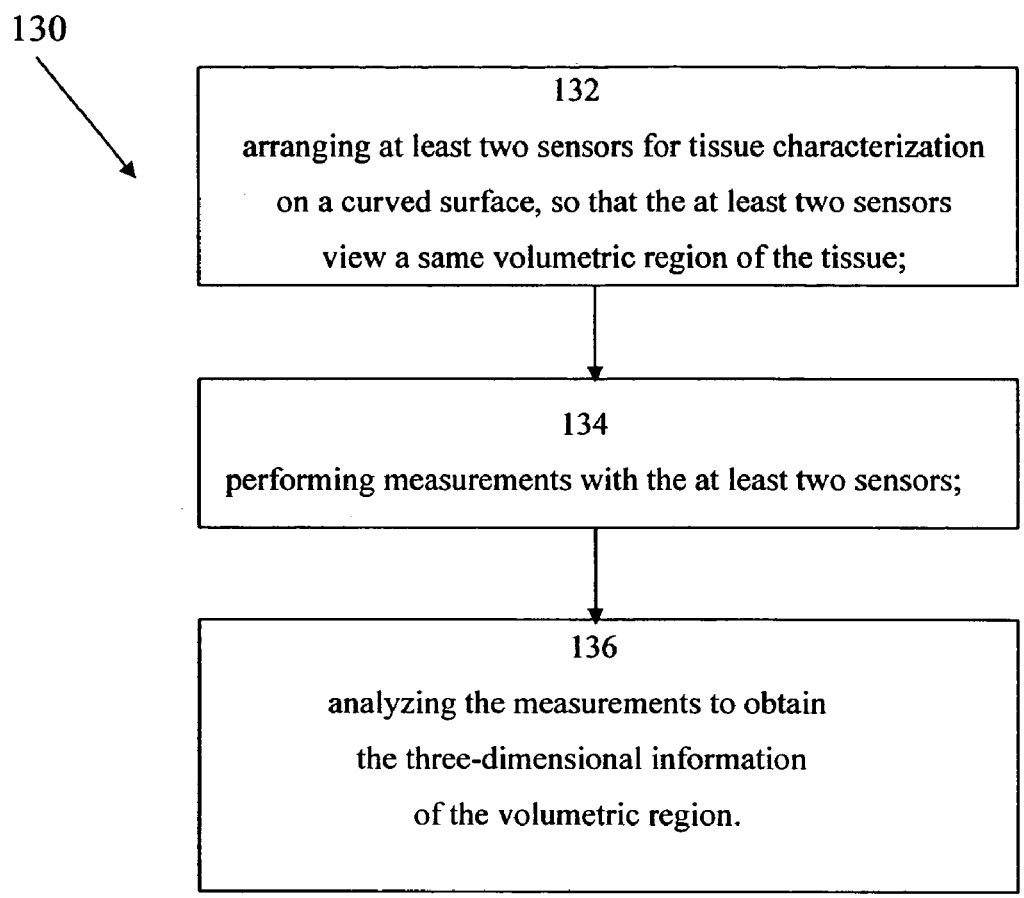

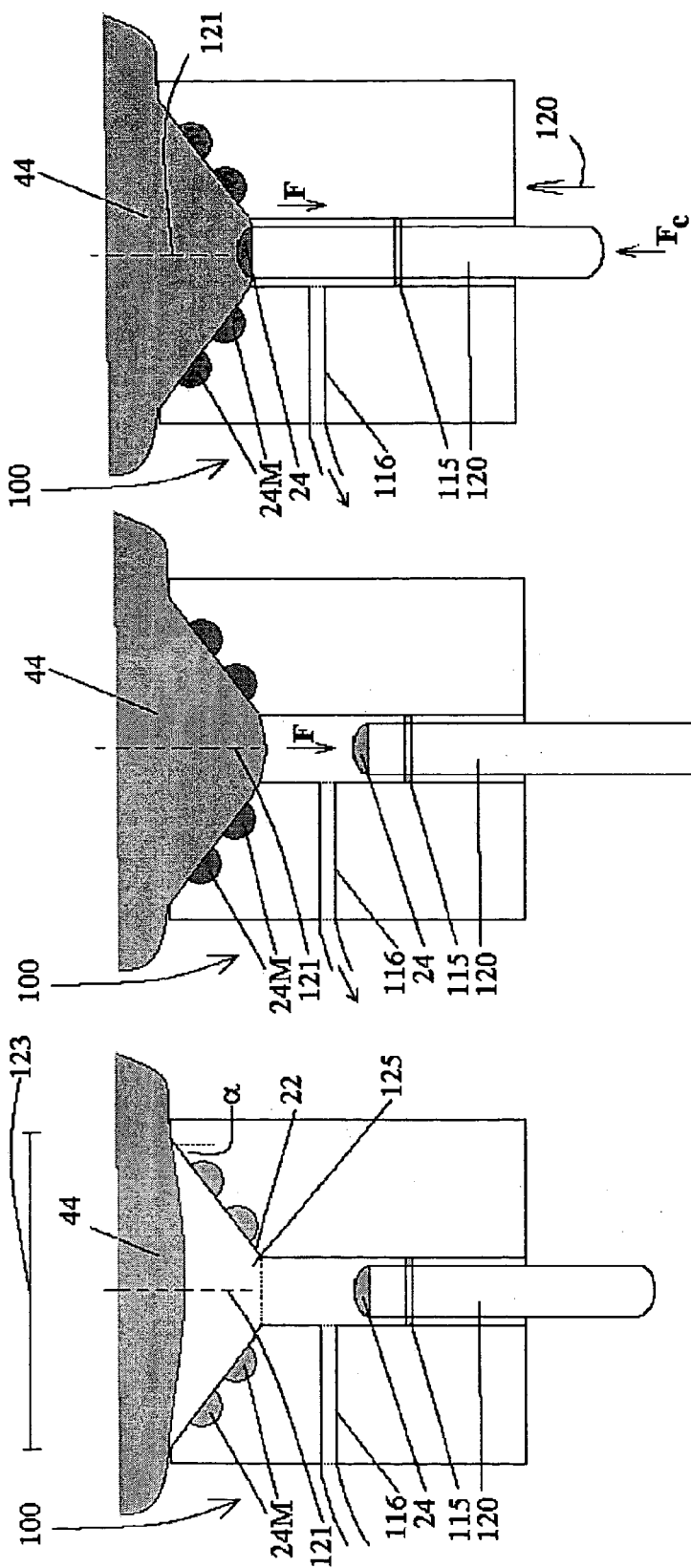

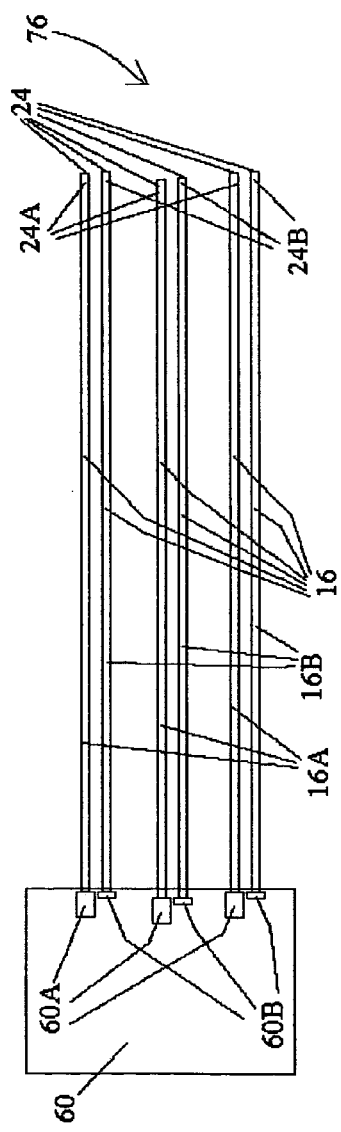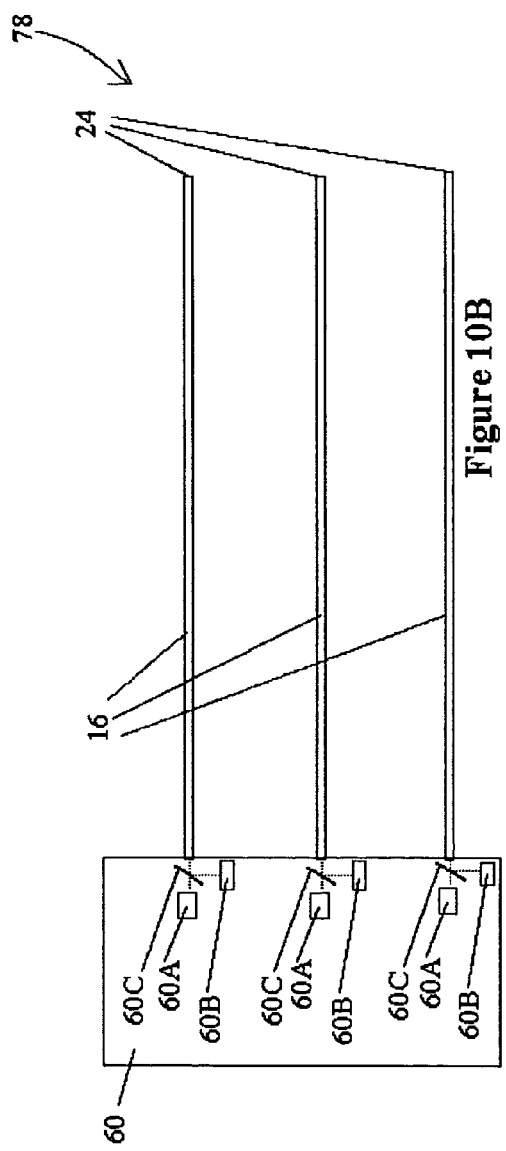

TISSUE-CHARACTERIZATION PROBE WITH EFFECTIVE SENSOR-TO-TISSUE CONTACT

CROSS-REFERENCE TO RELATED APPLICATIONS

The present invention is a continuation in part of U.S. patent application Ser. No. 11/196,732, filed on Aug. 4, 2005, whose disclosure is incorporated herein by reference.

FIELD AND BACKGROUND OF THE INVENTION

The present invention relates to local tissue characterization and more particularly, to a tissue-characterization probe with effective sensor-to-tissue contact. The probe is further adapted for providing three-dimensional information.

A large number of techniques and sensors are available today for tissue characterization, for example, to determine the presence of abnormal tissue, such as cancerous or precancerous tissue. These may be incorporated into hand-held probes or miniature probes, adapted for insertion into a body lumen or for use in minimally invasive surgery. While the operating principles of different tissue characterization sensors differ, effective contact between the sensor and the tissue is often essential for reliable results. For example, the presence of air bubbles between an ultrasound sensor and the tissue will interfere with ultrasound measurements. Similarly, a liquid layer may interfere with an optical spectroscopy sensor.

The use of suction, for engaging a medical instrument to a tissue, is known. For example, U.S. Pat. No. 5,927,284, to Borst, entitled, "A Method and Apparatus for Temporarily Immobilizing a Local Area of Tissue," whose disclosure is incorporated herein by reference, describes temporarily immobilizing a local area of heart tissue to permit surgery on a coronary vessel in that area without significant deterioration of the pumping function of the beating heart. The local area of heart tissue is immobilized to a degree sufficient to permit minimally invasive or micro-surgery on that area of the heart. A suction device is used to accomplish the immobilization. The suction device is coupled to a source of negative pressure. The suction device has a series of suction ports on one surface. Suction through the device causes suction to be maintained at the ports. The device is shaped to conform to the surface of the heart. Thus, when the device is placed on the surface of the heart and suction is created, the suction through the ports engages the surface of the heart. The suction device is further fixed or immobilized to a stationary object, such as an operating table or a sternal or rib retractor. Thus, the local area of the heart near the suction device is temporarily fixed or immobilized relative to the stationary object while suction is maintained. In this fashion, the coronary artery may be immobilized, even though the heart itself is still beating so that a bypass graft may be performed. In addition, the suction device may be used in either a conventional, open-chest environment or in a minimally-invasive, endoscopic environment.

Additionally, U.S. Pat. No. 6,728,565, to Wendlandt, entitled, "Diagnostic Catheter Using a Vacuum for Tissue Positioning," whose disclosure is incorporated herein by reference, describes the use of a diagnostic catheter, associated with a vacuum source, for attaching a sensor to a tissue surface. The method includes inserting a catheter with a sensor at its distal end into the body of a patient, applying suction through the catheter, to draw tissue into a predetermined sensing position for the sensor, and analyzing the tissue with the sensor. The degree of vacuum may be adjusted, so that only the required amount of force is used to maintain contact between the sensor or sensors and the tissue being analyzed.

U.S. Pat. No. 6,090,041, to Clark, entitled, "Vacuum Actuated Surgical Retractor and Methods," whose disclosure is incorporated herein by reference, describes a surgical retractor for retracting body tissue or organs, using suction. The surgical retractor includes an end piece adapted for sealing engagement with body tissue, the end piece having at least one suction port therein, the at least one suction port operably linked to at least one Vacuum line. Suction supplied to the at least one suction port may be controlled by a vacuum control unit. Retractors of the invention may be provided in a range of shapes and sizes, according to the intended application or tissue to be retracted. A method for making a vacuum actuated retractor of the invention is disclosed, together with a method for automatically retracting body tissue.

U.S. Pat. No. 6,500,112, to Khouri, entitled, "Vacuum Dome with Supporting Rim and Rim Cushion," whose disclosure is incorporated herein by reference, describes the use of vacuum for tissue stretching, to enlarge a soft tissue, for example after a breast surgery, or to correct a deformity. It utilizes a generally rigid dome, capable of withstanding a pressure differential, with a rim cushion underlying the rim of the dome, for supporting the rim against the patient's skin surface. The rim may be generally wider than the dome in order to distribute the attendant forces across a greater surface and avoid tissue damage. A sticky sole underlies the rim cushion and seals the rim cushion to the patient's skin, to thereby preserve the vacuum within the dome. The sticky sole may be any adhesive material or may be achieved through the use of an appropriate material for the rim cushion itself. Unlike the other references, described hereinabove, in U.S. Pat. No. 6,500,112, the vacuum is used for its therapeutic effect, i.e., tissue stretching, to enlarge a soft tissue or to correct a deformity, rather than as means for attaching another instrument.

While the aforementioned devices relate to engagement with a tissue, they do not address the quality of the engagement surface. There is thus a need for devices and methods for ensuring effective contact between a tissue-characterization sensor and a tissue, free of air, liquid and foreign matter.

SUMMARY OF THE INVENTION

The present relates to a device for tissue-characterization, designed for effective sensor-to-tissue contact. The device includes an element, having a rigid surface of a linear cross-section, on which at least one sensor is arranged, and a mechanism for applying a force to a soft tissue, the line of force being at an acute angle with the rigid surface, for stretching or stretching and pushing the soft tissue against the rigid surface, thus achieving effective contact between the tissue and the at least one sensor. In consequence, the accuracy of the sensing is improved. In accordance with another embodiment, a plurality of sensors is employed, arranged along a curved element, for providing three-dimensional information regarding the tissue, for example, by small-scale computerized tomography.

There is thus provided, in accordance with an aspect of the present invention, a device, comprising:

an element, which defines a rigid surface of a linear cross-section, configured to make contact with a tissue;

at least one sensor, in physical contact with the rigid surface; and a mechanism, adapted for applying a force to the tissue, the line of force being at an acute angle with the rigid surface, for stretching the tissue against the rigid surface, thus achieving effective contact between the tissue and the rigid surface.

Additionally, the stretching further includes stretching and pushing.

Furthermore, the acute angle is between 30 degrees and 60 degrees.

Additionally, the effective contact is a contact level of at least 95%.

Furthermore, the effective contact is a contact level of at least 99%.

Additionally, the effective contact is a contact level of at least 99.5%.

Furthermore, the effective contact is a contact level of at least 99.8%.

Additionally, the sensor is an irradiative sensor of a wavelength $\lambda$, and an average distance t1, between external-most surfaces of the tissue and the sensor, is such that $t1<\lambda/3$.

Furthermore, the sensor is an irradiative sensor of a wavelength $\lambda$, and an average distance t1 between external-most surfaces of the tissue and the sensor is such that $t1<\lambda/10$.

Additionally, the sensor is an irradiative sensor of a wavelength $\lambda$, and an average distance t1, between external-most surfaces of the tissue and the sensor is such that $t1<\lambda/100$.

Alternatively, an average distance t1, between external-most surfaces of the tissue and the sensor, is less than 500 Angstroms.

Additionally, an average distance t1, between external-most surfaces of the tissue and the sensor, is less than 50 Angstroms.

Furthermore, an average distance t1, between external-most surfaces of the tissue and the sensor, is less than 5 Angstroms.

Additionally, the at least one sensor is an irradiative sensor, selected from the group consisting of an optical sensor, an X-ray sensor, an RF sensor, a MW sensor, an infrared thermography sensor, and an ultrasound sensor.

Furthermore, the at least one sensor is selected from the group consisting of an MR sensor, an impedance sensor, a temperature sensor, a biosensor, a chemical sensor, a radioactive-emission sensor, a nonirradiative RF sensor, and a mechanical sensor.

Additionally, the device further comprises a plurality of sensors.

Alternatively, the at least one sensor includes at least two different types of sensors.

Additionally, the at least one sensor includes at least two different types of sensors, selected from the group consisting of optical sensors, X-ray sensors, RF sensors, MW sensors, infrared thermography sensors, ultrasound sensors, MR sensors, impedance sensors, temperature sensors, biosensors, chemical sensors, radioactive-emission sensors, mechanical sensors, and nonirradiative RF sensors.

Furthermore, the element defines a curvature for obtaining three-dimensional information, and further wherein the plurality of sensors includes at least two sensors, arranged along the curvature, each defining a viewing angle, the at least two sensors sharing a portion of their viewing angles so as to obtain three-dimensional information.

Additionally, the plurality of sensors includes at least four sensors, arranged as at least two pairs of sensors, each pair being of substantially identical sensors, and each pair representing a different type of sensor, for providing three-dimensional information by at least two modalities.

Furthermore, the three-dimensional information includes small-scale computerized tomography.

Additionally, the mechanism is suction.

Alternatively, the mechanism is tweezers-like.

Alternatively, the mechanism exerts physical pressure on the tissue.

There is thus also provided, in accordance with another aspect of the present invention, a tissue-characterization probe, comprising:

a housing, which defines proximal and distal ends, with respect to a tissue;

an element, at the proximal end of the probe, the element defining a rigid surface of a linear cross-section, configured to make contact with the tissue;

a mechanism, adapted for applying a force to the tissue, the line of force being at an acute angle with the rigid surface, for stretching the tissue against the rigid surface, thus achieving effective contact between the tissue and the rigid surface;

at least one sensor, in physical contact with the rigid surface; and at least one signal communication line, for providing communication between a signal analyzer and the at least one sensor.

Additionally, the mechanism is suction.

Furthermore, a pump, which provides the suction, is arranged within the housing.

Additionally, the suction is provided by a channel, arranged within the housing and in communication with an external vacuum source.

Furthermore, the channel is operative to drain off tissue fluids.

Additionally, the probe is configured for an application, selected from the group consisting of extracorporeal application to a skin, intracorporeal insertion through a body lumen, intracorporeal insertion for a minimally invasive procedure, and application to subcutaneous tissue, during open surgery.

There is thus provided, in accordance with yet another aspect of the present invention, a tissue-characterization system, comprising:

a housing, which defines proximal and distal ends, with respect to a tissue;

an element, at the proximal end of the probe, the element defining a rigid surface of a linear cross-section, configured to make contact with a tissue;

a mechanism, adapted for applying a force to the tissue, the line of force being at an acute angle with the rigid surface, for stretching the tissue against the rigid surface, thus achieving effective contact between the tissue and the rigid surface;

at least one sensor, in physical contact with the rigid surface;

a signal analyzer; and at least one signal communication line, for providing communication between the signal analyzer and the at least one sensor.

There is thus provided, in accordance with still another aspect of the present invention, a method of tissue characterization, comprising:

providing a tissue characterization probe, which comprises:

an element, which defines a rigid surface of a linear cross-section, configured to make contact with a tissue;

at least one sensor, in physical contact with the rigid surface; and a mechanism, adapted for applying a force to the tissue, the line of force being at an acute angle with the rigid surface, for stretching the tissue against the rigid surface, thus achieving effective contact between the tissue and the rigid surface;

applying a force to the tissue, the line of force being at an acute angle with the rigid surface, for stretching the tissue against the rigid surface, thus achieving effective contact between the tissue and the rigid surface; and characterizing the tissue with the at least one sensor.

There is thus provided, in accordance with yet another aspect of the present invention, a device, comprising:

an element, which defines a surface with a curvature in a first direction, the curvature being at least greater than that of a circle having a diameter of 8 cm; and at least two sensors, arranged along the curvature, each defining a viewing angle into a volume, the at least two sensors sharing a portion of their viewing angles so as to obtain three-dimensional information of the volume.

Additionally, the curvature is greater than that of a circle having a diameter of about 6 cm.

Furthermore, the curvature is greater than that of a circle having a diameter of about 4 cm.

Additionally, the curvature is greater than that of a circle having a diameter of about 2 cm.

Furthermore, the curvature is greater than that of a circle having a diameter of about 1 cm.

Additionally, the curvature is greater than that of a circle having a diameter of about 0.8 cm.

Additionally, the at least two sensors include at least four sensors, arranged as at least two pairs of sensors, each pair being of substantially identical sensors arranged along the curvature, and each pair representing a different type of sensors, for providing three-dimensional information by at least two modalities.

There is thus provided, in accordance with still another aspect of the present invention, a tissue-characterization probe, comprising:

a housing, which defines proximal and distal ends, with respect to a tissue, an element, which defines a surface with a curvature in a first direction, the curvature being at least greater than that of a circle having a diameter of 8 cm;

at least two sensors, arranged along the curvature, each defining a viewing angle into a volume, the at least two sensors sharing a portion of their viewing angles so as to obtain three-dimensional information of the volume; and a signal communication architecture, for providing communication between a signal analyzer and the at least two sensors.

Additionally, the probe is configured for insertion to a body lumen.

Alternatively, the probe is configured for insertion for insertion intracorporeally, for minimally invasive procedures.

Alternatively, the probe is configured for insertion for insertion intracorporeally, during open surgery.

Alternatively, the probe is configured for extracorporeal application, wherein the tissue is a skin.

There is thus provided, in accordance with still another aspect of the present invention, a tissue-characterization system, comprising:

a housing, which defines proximal and distal ends, with respect to a tissue, an element, which defines a surface with a curvature in a first direction, the curvature being at least greater than that of a circle having a diameter of 8 cm; and at least two sensors, arranged along the curvature, each defining a viewing angle into a volume, the at least two sensors sharing a portion of their viewing angles so as to obtain three-dimensional information of the volume;

a signal analyzer; and a signal communication architecture, for providing communication between a signal analyzer and one of the at least two sensors.

There is thus provided, in accordance with yet another aspect of the present invention, a method of tissue characterization, for obtaining three-dimensional information of a volumetric region within the tissue, comprising:

providing an element, which defined a surface with a curvature in a first direction, having a diameter which is less than 8 cm; and arranging at least two sensors on the curvature, each defining a viewing angle into a volumetric region, the at least two sensors sharing a portion of their viewing angles;

performing measurements with the at least two sensors; and analyzing the measurements to obtain the three-dimensional information of the volume.

There is thus provided, in accordance with still another aspect of the present invention, a method of tissue characterization, comprising:

providing an element, which defines a surface with a curvature in a first direction, the curvature having a diameter which is less than 8 cm;

arranging at least two pairs of sensors along the curvature, each pair being of substantially identical sensors, and each pair representing a different type of sensors, for providing three-dimensional information by at least two modalities;

performing measurements with the at least two pairs of sensors; and analyzing the measurements to obtain the three-dimensional information of a volume, by the at least two modalities.

There is thus provided, in accordance with yet another aspect of the present invention, a device for tissue characterization, comprising:

a structure, formed of a rigid surface configured as a truncated cone, having a first cross-sectional configuration defining a diameter and having a second cross-sectional configuration defining an axis;

a first mechanism, associated with the structure, configured for causing a force to be exerted on a tissue, in a direction, along the axis, at an acute angle $\alpha$ to the rigid surface, for fixing the tissue to the structure, so as to substantially immobilize the tissue; and a second mechanism, associated with the structure, configured for pressing at least one piston sensor against an external surface of the immobilized tissue, thereby exerting a counter force on the immobilized tissue, wherein at least a component of the force is in opposition to at least a component of the counter force, forcing the immobilized tissue against the at least one piston sensor, and forcing the at least one piston sensor against the immobilized tissue, bringing about an effective contact between the at least one piston sensor and the immobilized tissue.

Additionally, the at least one piston sensor includes at least two piston sensors of a same type.

Furthermore, the at least one piston sensor includes at least two piston sensors of different types.

Additionally, the probe includes at least one cone sensor, arranged on the rigid surface.

Furthermore, the probe includes at least two cone sensors, arranged on the rigid surface of the linear cross section.

Additionally, wherein the at least two cone sensors are arranged along the curvature, each cone sensor defining a viewing angle, the at least two cone sensors sharing a portion of their viewing angles so as to obtain three-dimensional information.

Furthermore, the at least one cone sensor includes at least four cone sensors, arranged as at least two pairs of cone sensors, each pair being of substantially identical cone sensors, and each pair representing a different type of cone sensor, for providing three-dimensional information by at least two modalities.

Additionally, wherein the first mechanism is a suction source, for fixing and substantially immobilizing the tissue, by suction.

There is thus provided, in accordance with still another aspect of the present invention, a tissue characterization probe, comprising:

a housing;

a structure, formed of a rigid surface of a conical cross-section, having a diameter in a first direction and an axis in a second direction, and a rigid surface;

a first mechanism, associated with the structure, configured for exerting a force on a tissue, in the second direction, along the axis, at an acute angle α to the rigid surface, for fixing the tissue to the structure, so as to substantially immobilize the tissue; and a second mechanism, associated with the structure, configured for pressing at least one piston sensor against an external surface of the immobilized tissue, thereby exerting a counter force on the immobilized tissue, wherein at least a component of the force is in opposition to at least a component of the counter force, forcing the immobilized tissue against the at least, one piston sensor, and forcing the piston sensor against the immobilized tissue, bringing about an effective contact between the at least one piston sensor and the immobilized tissue; and a signal communication architecture, for providing communication between a signal analyzer and the at least one piston sensor.

Additionally, the probe is configured for an application, selected from the group consisting of extracorporeal application to a skin, intracorporeal insertion through a body lumen, intracorporeal insertion for a minimally invasive procedure, and application to subcutaneous tissue, during open surgery.

There is thus provided, in accordance with still another aspect of the present invention, a system for tissue characterization, comprising:

a housing;

a structure, formed of a rigid surface of a conical cross-section, having a diameter in a first direction and an axis in a second direction, and a rigid surface;

a first mechanism, associated with the structure, configured for exerting a force on a tissue, in the second direction, along the axis, at an acute angle λ to the rigid surface, for fixing the tissue to the structure, so as to substantially immobilize the tissue; and a second mechanism, associated with the structure, configured for pressing at least one piston sensor against an external surface of the immobilized tissue, thereby exerting a counter force on the immobilized tissue, wherein at least a component of the force is in opposition to at least a component of the counter force, forcing the immobilized tissue against the at least one piston sensor, and forcing the piston sensor against the immobilized tissue, bringing about an effective contact between the at least one piston sensor and the immobilized tissue;

a signal analyzer; and a signal communication architecture, for providing communication between the signal analyzer and the at least one piston sensor.

There is thus provided, in accordance with yet another aspect of the present invention, a method for tissue characterization, comprising:

providing a device for tissue characterization, which comprises:

a structure, formed of a rigid surface of a conical cross-section, having a diameter in a first direction and an axis in a second direction, and a rigid surface;

a first mechanism, associated with the structure, configured for applying a force to on a tissue, in a second direction along the axis, at an acute angle α to the rigid surface, for fixing the tissue to the structure, so as to substantially immobilize the tissue; and a second mechanism, associated with the structure, configured for pressing at least one piston sensor against an external surface of the immobilized tissue, thereby exerting a counter force on the immobilized tissue, wherein at least a component of the force is in opposition to at least a component of the counter force, forcing the immobilized tissue against the at least one piston sensor, and forcing the at least one piston sensor against the immobilized tissue, bringing about an effective contact between the at least one piston sensor and the immobilized tissue;

fixing the tissue to the structure, thus substantially immobilizing the tissue; and pressing the at least one piston sensor against the external surface of the immobilized tissue, thereby exerting the counter force on the immobilized tissue, wherein at least the component of the force is in opposition to at least the component of the counter force, forcing the immobilized tissue against the at least one piston sensor, and forcing the at least one piston sensor against the immobilized tissue, thus bringing about the effective contact between the at least one piston sensor and the immobilized tissue; and characterizing the tissue with the at least one piston sensor.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and are not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-1G, and 1N schematically illustrate a longitudinal cross-section of a device, for effective sensor-to-tissue contact, in accordance with some embodiments of the present invention;

FIGS. 1H-1L schematically illustrate situations of potentially poor contact between a tissue and a device, as seen in a longitudinal cross-section, in accordance with the understanding the present invention;

FIG. 1M schematically illustrates an effective contact between a tissue and a device, as seen in a longitudinal cross-section, in accordance with the embodiments of the present invention;

FIGS. 1O-1V schematically illustrate various transverse and longitudinal cross sections of a device, in accordance with some embodiments of the present invention.

FIGS. 2A-2E schematically illustrate, in longitudinal cross-sectional view, a probe for tissue characterization, constructed with the device of the present invention;

FIGS. 7A-7C schematically illustrate another configuration for effective contact, in accordance with an embodiment of the present invention;

FIGS. 10A and 10B schematically illustrate optical sensor constructions, in accordance with some embodiments of the present invention.

DESCRIPTION OF THE PREFERRED EMBODIMENTS

Figure 1G:
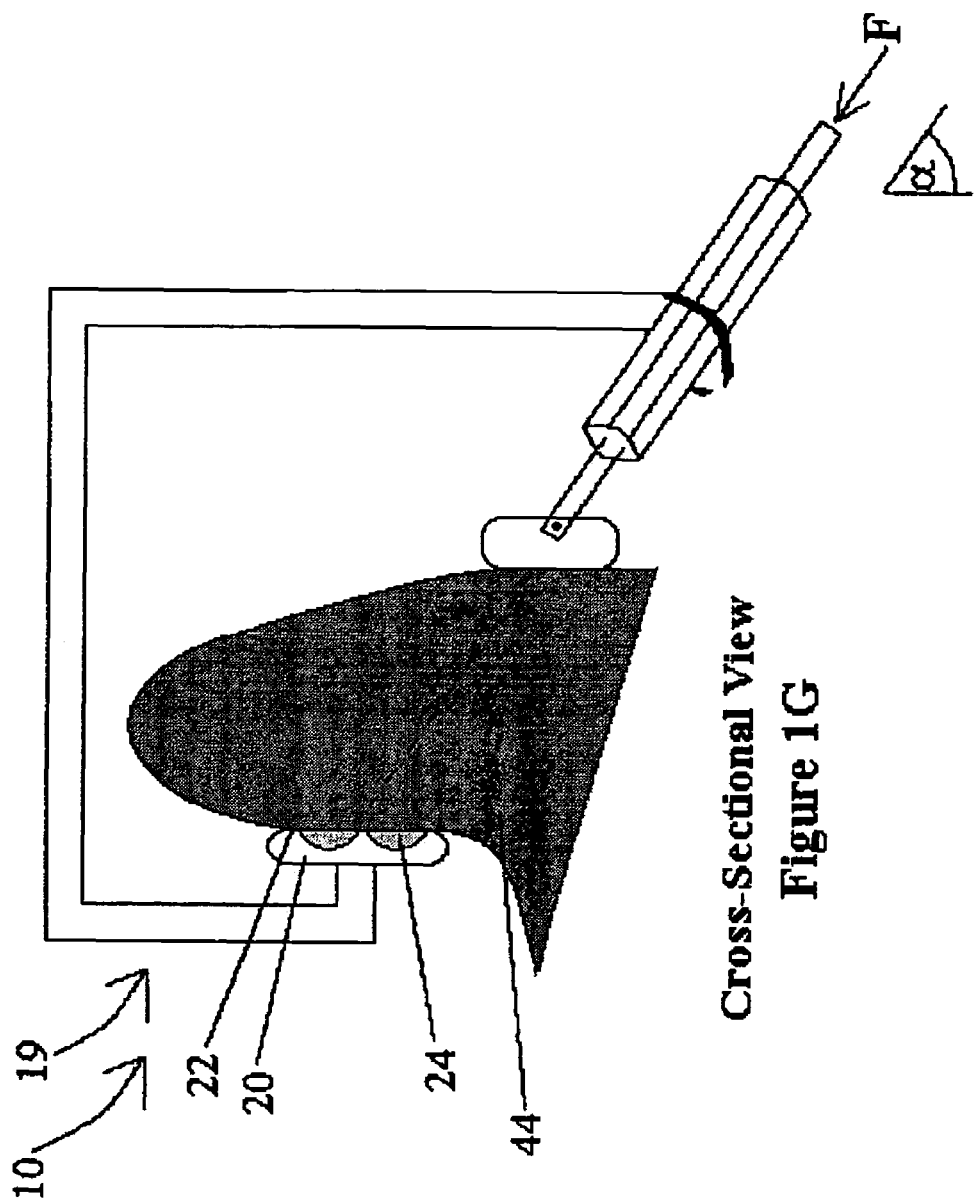

The present invention relates to a device for tissue-characterization, designed for effective sensor-to-tissue contact. The device includes an element, having a rigid surface of a linear cross-section, on which at least one sensor is arranged, and a mechanism for applying a force to a soft tissue, the line of force being at an acute angle with the rigid surface, for stretching or stretching and pushing the soft tissue against the rigid surface, thus achieving effective contact between the tissue and the at least one sensor. In consequence, the accuracy of the sensing is improved. In accordance with another embodiment, a plurality of sensors is employed, arranged along a curved element, for providing three-dimensional information regarding the tissue, for example, by small-scale computerized tomography.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The principles and operation of the device for tissue-characterization, according to some embodiments of the present invention, may be better understood with reference to the drawings and accompanying descriptions.

Referring now to the drawings, FIGS. 1A-1G and 1N schematically illustrate a longitudinal cross-section of a device 10, for effective sensor-to-tissue contact, in accordance with some embodiments of the present invention.

Accordingly, the device 10 includes an element 20, configured to make contact with a tissue 44, which is at a proximal end 29. As seen in FIGS. 1A-1E, and 1N the element 20 may be shaped as a cone, having a base 26. However, as seen in FIG. 1F, other shapes may similarly be used. Some of these are described hereinbelow, in conjunction with FIGS. 1O-1V.

The tissue 44 is a soft tissue, such as the tissue of muscle, skin, fat, internal organs, internal interfaces and the like, which generally yields under pressure.

Preferably, the element 20 includes a section of a length L, having a linear cross section, and forming a rigid surface 22. The contact with the tissue 44 is made along the rigid surface 22 of the preferably linear cross section.

Additionally, the device 10 includes at least one sensor 24, associated with the rigid surface 22. A plurality of sensors 24 may be employed. The at least one sensor 24 may be embedded within or mounted on the rigid surface 22.

Furthermore, the device 10 includes a mechanism 19, adapted for applying a force F to the tissue 44, the line of force being at an acute angle α to the rigid surface 22, for stretching or stretching and pushing the tissue 44 against the rigid surface 22, thus achieving effective contact between the tissue 44 and the rigid surface 22. In consequence, effective contact between the tissue 44 and the at least one sensor 24 is formed, and the accuracy of the sensing is improved.

FIG. 1B illustrates the angular relation between the force F and the rigid surface 22. Intuitively, one may observe that were the force F parallel with or perpendicular to the rigid surface 22, the desired stretching of the tissue 44 against the rigid surface 22 would not happen. The acute angle α between the line of force F and the rigid surface 22 is essential for the practice of the present invention. Preferably, the acute angle α is between about 30 degrees and about 60 degrees, yet other values of acute angles may also be used.

Additionally, one may observe that were the surface 22 curved, the stretching of the tissue 44 against the rigid surface 22 would not be uniform along the section of length L. Thus in accordance with the preferred embodiment of the present invention, the surface 22 has a linear cross section.

As seen in FIG. 1C, the mechanism 19, which provides the force F, may be a vacuum source 32, for essentially sucking the tissue 44 into the element 20.

FIG. 1N illustrates a similar situation, but with a single sensor 24, in accordance with some embodiments of the present invention.

Alternatively, as seen in FIG. 1D, the mechanism 19 may be a mechanical tool, for example, a tweezers-like tool 13, for pulling the tissue 44 into the element 20.

Alternatively still, as seen in FIGS. 1E and 1F, the mechanism 19 may be another mechanical tool, for example, a mallet-like tool 17, for pressing the tissue 44 into the element 20.

FIG. 1G schematically illustrates still another example of the mechanism 19, for applying the force F to the tissue 44, at the acute angle λ to the rigid surface 22, wherein the rigid surface 22 may be a flat plate. The mechanism 19 may be, for example, a piston-cylinder configuration, arranged at the angle λ to the flat plate, operative as the element 20, and having the rigid surface 22, in which the sensors 24 are embedded.

Referring further to the drawings, FIGS. 1H-1L schematically illustrate situations of potentially poor contact between the tissue 44 and the rigid surface 22 of the element 20, in which the sensors 24 are embedded, as seen in a longitudinal cross-section of the device 10, in accordance with the understanding of the present invention. In contrast, FIG. 1M schematically illustrates an effective contact between the tissue and the device 10, as seen in the longitudinal cross-section, in accordance with embodiments of the present invention.

FIG. 1H is a cross-sectional view of an interface 45, between the rigid surface 22 of the element 20 and the at least one sensor 24, on the one hand, and the tissue 44, on the other. A section 43 is marked and enlarged in FIGS. 1I-1M, hereinbelow.

FIG. 1I provides a cross-sectional view of the interface 45, at the section 43, showing bubbles 46 of air or fluids, and (or) inclusions 47 of foreign matter, which reduce and otherwise deteriorate the contact area between the tissue 44 and the at least one sensor 24, along the interface 45.

FIG. 1J also provides the cross-sectional view of the interface 45, at the section 43, showing that tissue folds 48, possibly with bubbles 46 and (or) inclusions 47, may also reduce and otherwise deteriorate the contact area between the tissue 44 and the at least one sensor 24, along the interface 45.

FIG. 1K provides a view of the interface 45, at the section 43, from the direction of an arrow 11 of FIG. 1H, showing the bubbles 46 and the inclusions 47, deteriorating the contact at the interface 45.

Defining:
Actual contact area A(actual), as the actual contact area between the rigid surface 22 and the tissue 44;
Overall contact area A(interface), as the whole area of the interface 45; and
Bubble and inclusions area A(bubbles and inclusions), as an area covered by bubbles 46 of air and (or) fluid, and (or) by inclusions 47 of foreign matter, one may calculate the actual contact area and a contact level, as follows:

$$A(actual) = A(interface) - A(bubbles\ and\ inclusions), \quad [1]$$

and, $$Contact\ Level = \frac{A(actual)}{A(interface)}. \quad [2]$$

Furthermore, one can quantify the effect of the bubbles 46 and the inclusions 47, and evaluate if the interface 45 is acceptable for tissue characterization, with a given sensor.

Embodiments of the present invention are aimed at achieving effective contact, which is a contact level of at least 95%. Preferably, the contact level is greater than 98%. More preferably, the contact level is at least 99.5%, and even at least 99.8%.

FIG. 1L provides the cross-sectional view of the interface 45, at the section 43, with reference to the at least one irradiative sensor 24, showing a situation where the edge surface of the irradiative sensor 24 and the external-most surface of the tissue 44 are slightly apart, by an average distance t, so that in effect, there are three interfaces 45A, 45B, and 45C, which may operate as three distinct reflective surfaces to incoming radiation 52. The first, the surface 45A, is the edge surface of the at least one sensor 24 (which is essentially the same as the rigid surface 22), the second, the surface 45B, is the external-most surface of the tissue 44, and the third, the surface 45C, is a joint interface of the edge surface of the at least one sensor 24 and the external-most surface of the tissue 44, when there is substantially complete contact. This effect may be important for radiation of a wavelength λ, for which the average distance t and the radiation wavelength λ are of a same order of magnitude, and in consequence, three reflections 54A, 54B, and 54C may be observed, from the interfaces 45A, 45B, 45C, respectively, rather than the single reflection 54C, of the joint interface.

In contrast with FIGS. 1H-1L, FIG. 1M schematically illustrates effective sensor-to-tissue contact, as a consequence of the balance of force diagram of FIG. 1G, in accordance with some embodiments of the present invention.

Accordingly, the interface 45 is substantially free of bubbles 46, foreign inclusions 47, and tissue folds 48, leading to effective contact, between the tissue 44 and the at least one sensor 24, the effective contact being defined as a contact level of at least 95%, preferably, at least 98%, and more preferably, at least 99.5% and even at least 99.8%.

Additionally, in accordance with embodiments of the present invention, which relate to sensors, operating with a wavelength λ, the effective contact may be further defined as a contact, for which the relationship between the wavelength λ and an average distance t1, the average distance after achieving effective contact, (see FIG. 1M) is such that $t1 < \lambda/3$, and preferably, $t1 < \lambda/10$, and more preferably, $t1 < \lambda/100$.

Additionally or alternatively, the effective contact may be defined in absolute terms. Accordingly, the average distance t1 is less than 500 Angstroms, preferably the average distance t1 is less than 50 Angstroms, and more preferably, the average distance t1 is less than 5 Angstroms.

Referring further to the drawings, FIGS. 1O-1V schematically illustrate various transverse and longitudinal cross sections of the element 20, in accordance with some embodiments of the present invention. All are associated with the rigid surface 22 of the linear cross section, arranged at the angle λ to the line of force F.

Accordingly, the transverse cross sections may be a circle (FIG. 1O), an ellipse (FIG. 1P), an arc (FIG. 1Q), or a line, associated with a flat plate (FIG. 1R), while the longitudinal cross sections may be a trapezoid (FIG. 1S), a triangle (FIG. 1T), a section of a trapezoid or triangle (FIG. 1U), or a line (FIG. 1V).

Thus, the overall shape of the element 20 may be a cone, with a circular or an elliptical cross section, with a base, or with no base, a section of a cone, or a flat plate.

Referring further to the drawings, FIGS. 2A-2E schematically illustrate a probe 50 for tissue characterization, constructed with the device 10 of the present invention. The probe 50 includes a housing 12, which includes the device 10 with the element 20 having a conical shape, as described hereinabove, in conjunction with FIGS. 1A-1V, and the at least one sensor 24. In accordance with an embodiment of the present invention, the probe 50 is hand-held, and may include a handle 14, for easy carrying. It will be appreciated that the probe 50 may also be employed for minimally invasive surgery, for example, for insertion via a trocar valve, or as an intracorporeal probe, adapted for insertion via a body lumen. The probe 50 may also be employed in open surgery, or for characterizing external skin.

As seen in FIG. 2A, in a longitudinal cross-sectional view, at least one signal communication line 16 leads from the at least one sensor 24 to a connector 36, preferably, at a distal end 21, associated with a cable 38, which provides power and signal communication with a signal-generation and analyzing station 70 described hereinbelow in conjunction with FIG. 3. A plurality of sensors 24 and a plurality of signal communication lines 16 may be employed. The at least one signal communication line may be a transmission line, for example, a coaxial cable, or an optical fiber.

As seen in FIG. 2B, in the longitudinal cross-sectional view, a battery 80 and a transceiver 82 may be employed, for example, located at the distal end 21, for wireless operation of the probe 50 and for wireless communication with the signal-generation and analyzer station 60. It will be appreciated that the battery 80 may be rechargeable.

The probe 50 may further include a pump 30, receiving power via a power line 37 and in fluid communication with the element 20, for providing suction to the cone 20, via a channel 32, leading to an orifice 34 in the element 20.

Figure 2C:
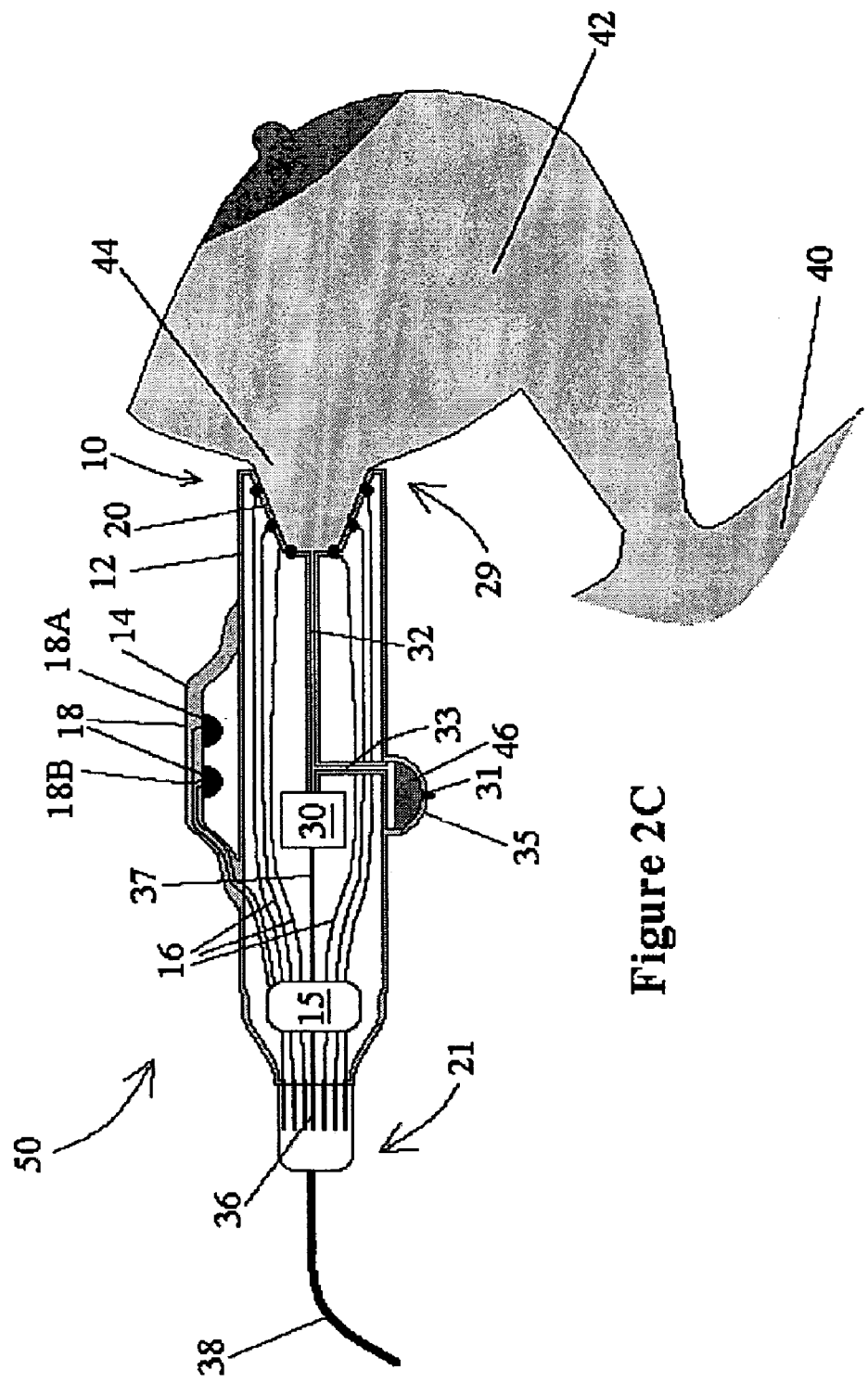

As seen in FIG. 2C, in the longitudinal cross-sectional view, the probe 50 may be used for characterizing the soft tissue 44, for example, of a breast 42 of a body 40, during open surgery. When suction is applied to the soft tissue 44, it is drawn into the element 20, maintaining effective contact with the at least one sensor 24.

Additionally, during surgery, fluids 46 may be drawn as well and directed by a channel 33 to a fluid trap 35, which may be emptied via a valve 31.

Figure 2D:
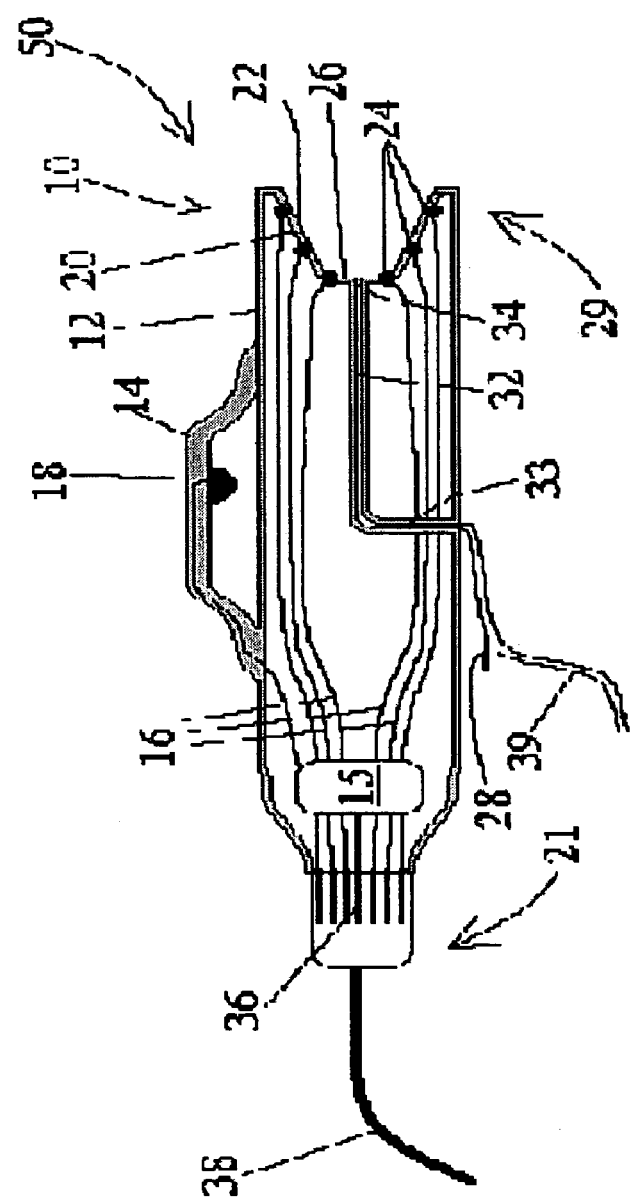

As seen in FIG. 2D, in the longitudinal cross-sectional view, a vacuum source (not shown) external to the probe 50 may be used, via a vacuum line 39. A sealing flap 28, along the vacuum line 39, may close when vacuum is applied, creating suction in the element 20. The vacuum line 39 may connect with a pump 30 and the fluid trap 35. Alternatively, the vacuum line 39 and the pump 30 may be external to the probe 50, as described hereinbelow, in conjunction with FIG. 3.

As seen in FIGS. 2A-2D, the probe 50 may further include at least one control switch 18, for initiating the measurement by the at least one sensor 24, or the plurality of sensors 24, and for controlling the pump 30 (FIGS. 2A-2C). Additionally, two control switches, 18A and 18B may be provided, one for operating the sensor or sensors 24 and the other for operating the pump 30. A junction 15 may be provided as a switching station, communicating with the at least one control switch 18, the signal communication lines 16, and the pump power line 37. It will be appreciated that the at least one sensor 24 or the plurality of sensors 24 may have a "standby" setting, and be set on standby, prior to operation.

FIG. 2E provides a perspective view of the probe 50, according to some embodiments of the present invention.

Figure 3:
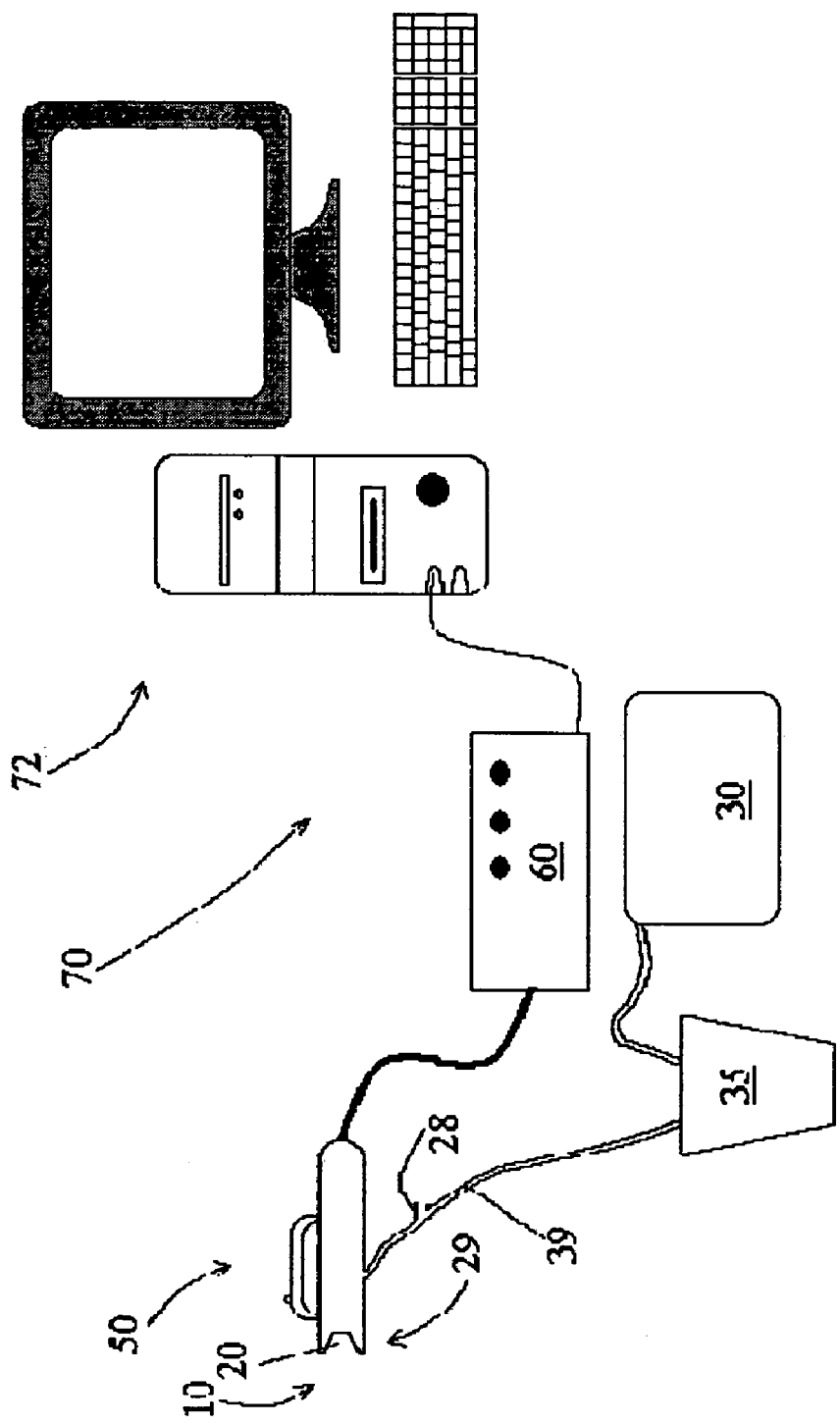
FIG. 3 schematically illustrates a system for tissue characterization, in accordance with some embodiments of the present invention.

Referring further to the drawings, FIG. 3 schematically illustrates a system 70 for tissue characterization, in accordance with some embodiments of the present invention. Preferably, the system 70 includes the probe 50, having the device 10 with the element 20 and at least one sensor 24, designed in accordance with some embodiments of the present invention. The probe 50 may be in fluid communication with an external fluid trap 35 and an external pump 30. Alternatively, these may be built into the probe 50.

Preferably, a signal generator and analyzer 60 communicates with the sensors 24, either via a cable 38 or in a wireless manner, as known. The signal generator and analyzer 60 may include a built-in computer, or may communicate with a computer station 72, which analyzes measurements performed by the probe 50. Alternatively, a miniaturized signal generator and analyzer 60 and possibly also a microcomputer (not shown) may be built into the probe 50. It will be appreciated that separate units may be employed for the signal generator and the signal analyzer. Additionally, some sensors are passive and do not require signal generators. For example, a temperature sensor, or a radioactive-emission sensor do not require signal generators.

Figure 4A:
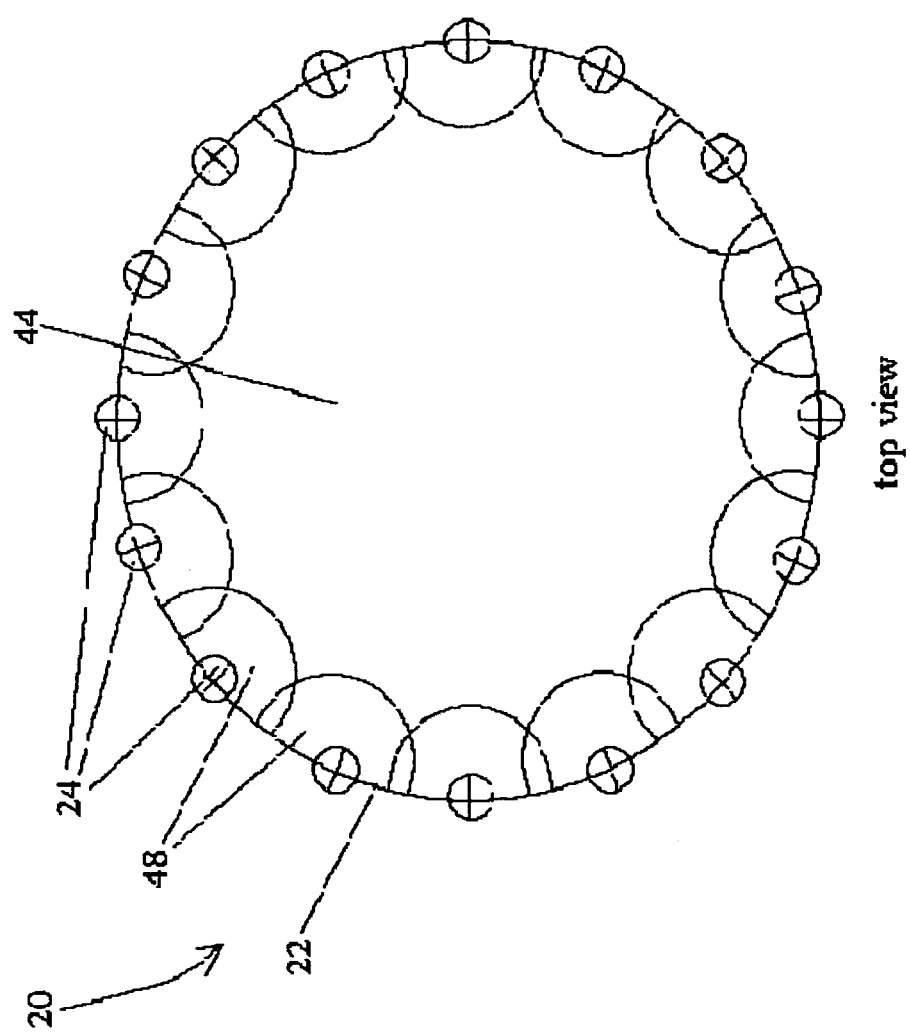
FIGS. 4A and 4B schematically illustrate a first arrangement of the sensors in the device, constructed in accordance with some embodiments of the present invention.
Figure 4B:
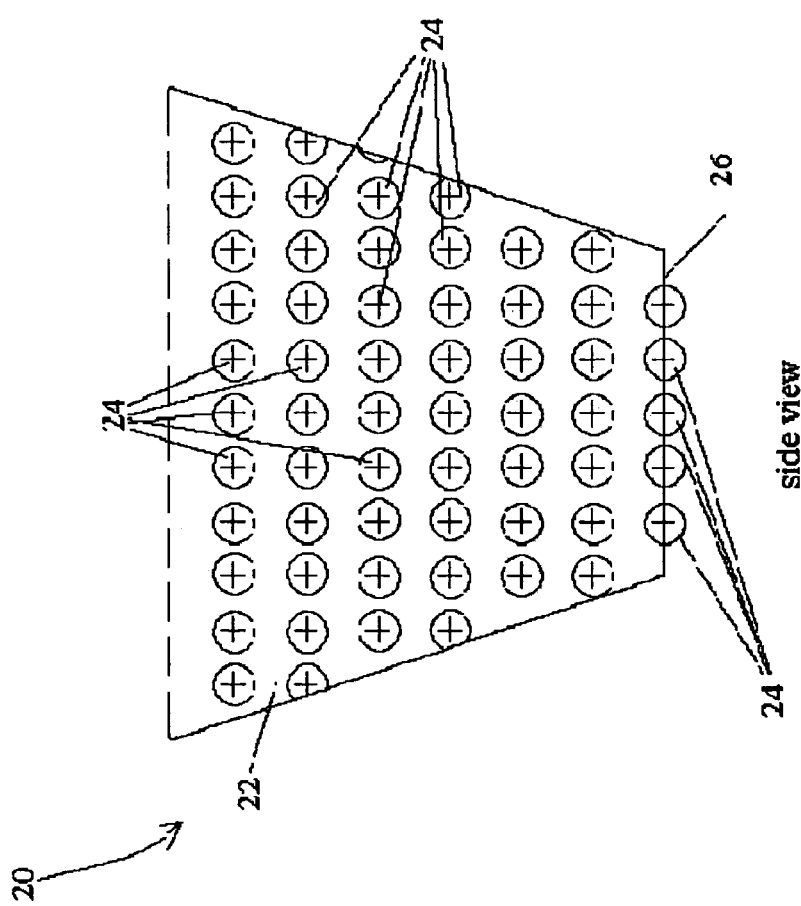

Referring further to the drawings, FIGS. 4A and 4B schematically illustrate a first arrangement of the at least one sensor 24 in the device 10, in accordance with some embodiments of the present invention. The element 20 may be shaped as a cone or as another shape having the rigid surface 22 of linear cross section, arranged at an acute angle to the applied force, and the at least one sensor 24 or the plurality of the sensors 24 may be embedded within or mounted on the rigid surface 22 of the element 20.

As seen in FIG. 4A, each of the sensors 24 characterizes the tissue 44, generally within a hemisphere-like volume 48, adjacent to it.

As seen in FIG. 4B, where the element 20 is shaped as a truncated cone, the sensors 24 may also be arranged along the base 26.

The at least one sensor 24 may be an irradiative sensor, such as an optical sensor, an X-ray sensor, an RF sensor, a MW sensor, an infrared thermography sensor, or an ultrasound sensor. Additionally or alternatively, the at least one sensor 24 may be an MR sensor, an impedance sensor, a temperature sensor, a biosensor, a chemical sensor, a radioactive-emission sensor, a mechanical sensor, a nonirradiative RF sensor, for example, as taught by commonly owned U.S. Patent Application 60/665,842, filed on Mar. 29, 2005, whose disclosure is incorporated herein by reference, and (or) another tissue characterization sensor, as known.

Figure 5:
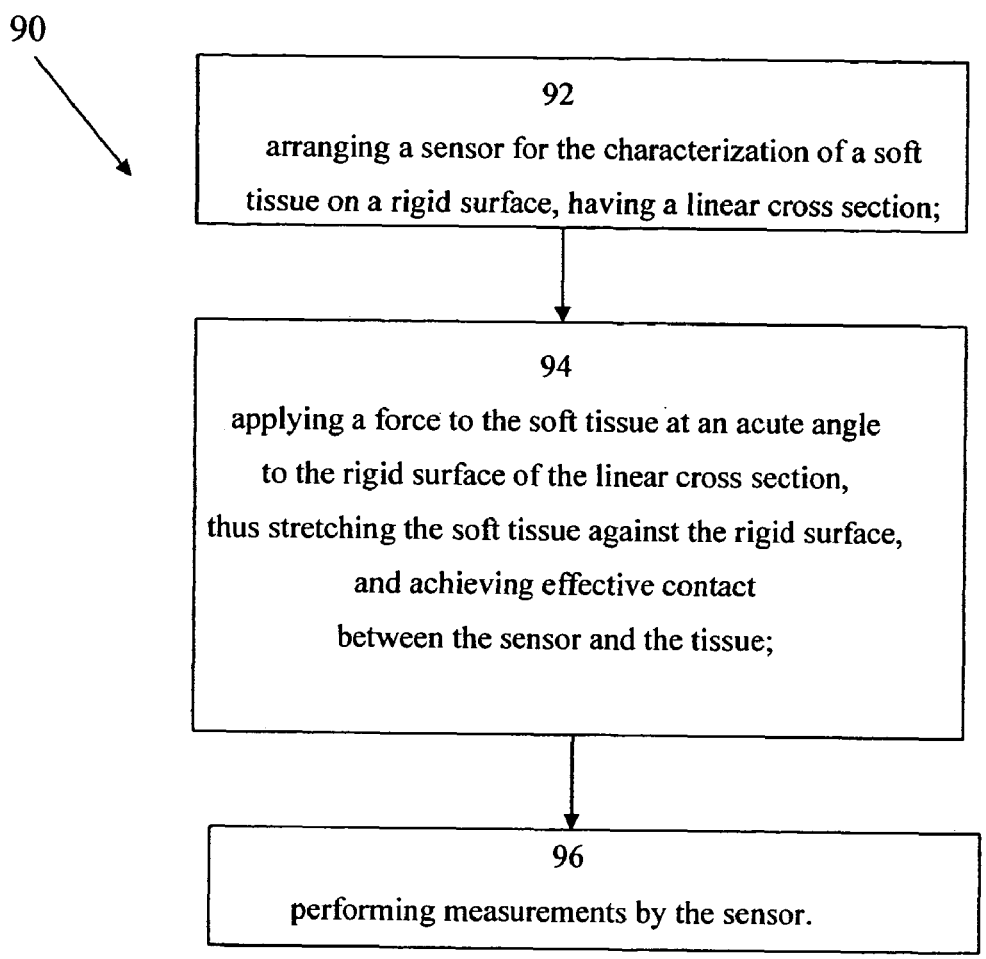
FIG. 5 is a flowchart illustrating a method of tissue characterization, by improving a contact level between a tissue and a sensor, in accordance with some embodiments of the present invention.

FIG. 5 schematically illustrates a method 90 for soft tissue characterization, by improving a contact level between the soft tissue 44 and the at least one sensor 24, in accordance with some embodiments of the present invention. The method 90 includes:

in a box 92: arranging at least one sensor for the characterization of a soft tissue on a rigid surface, having a linear cross section;

in a box 94: applying a force to the soft tissue at an acute angle to the rigid surface of the linear cross section, thus stretching or stretching and pushing the soft tissue against the rigid surface, and achieving effective contact between the sensor and the tissue; and in a box 96: performing measurements with the at least one sensor.

Referring further to the drawings, FIGS. 6A-6F schematically illustrate arrangements of a plurality of the sensors 24 in the device 10, for yielding three-dimensional information, for example, by small-scale computerized tomography, in accordance with some embodiments of the present invention.

Figure 6B:
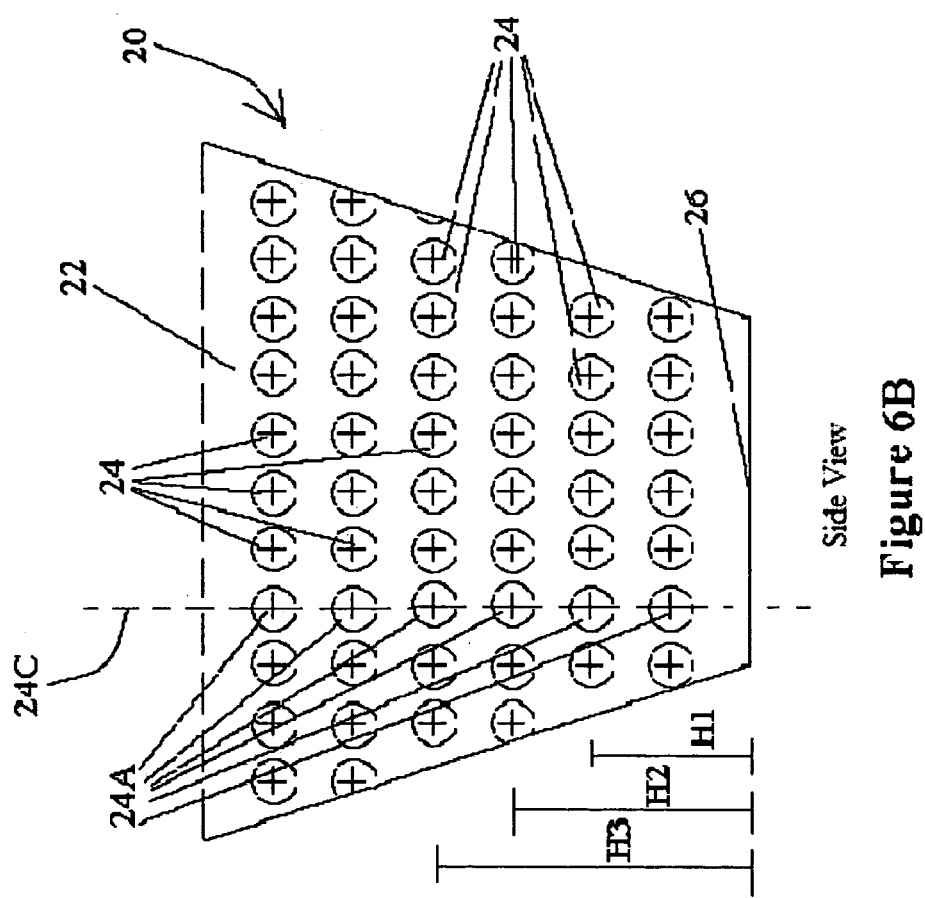
FIGS. 6A-6N schematically illustrate arrangements of the sensors in the device, for providing three-dimensional information, in accordance with further embodiments of the present invention.
FIG. 6O is a flowchart illustrating a method of tissue characterization in three-dimensions, with small-scale computerized tomography, in accordance with some embodiments of the present invention.

As seen in FIGS. 6A and 6B, the element 20 may be formed as a circular structure 20, such as the cone 20, with the plurality of the sensors 24, preferably arranged in circles around the internal circumference, embedded within or mounted on the rigid surface 22. Preferably, the sensors 24 of each circle are substantially aligned, along the vertical axis for example, forming a line 24C (FIG. 6B).

The sensors 24 are adapted for small-scale computerized tomography, which may be transmission small-scale computerized tomography, reflection small-scale computerized tomography, or a combination of the two. Preferably, each of the sensors 24, around the circumference, in turn, operates as a transmitting sensor 24A, sending out a signal 23, while the other sensors 24 operate as receiving sensors 24B, receiving signals 27 which may be transmitted, reflected, or a combination of transmitted and reflected. The position of the transmitting sensor 24A may change, for example by rotation, in a direction of an arrow 25. Alternatively, the position of the transmitting sensor 24A may change in another fashion, for example, randomly. In accordance with an embodiment of the present invention, the transmitting sensors 24A are aligned along the vertical line 24C, so as to image "slices of tissue."

It will be appreciated that other arrangements are similarly possible. For example, two or more sensors 24 in a circle may operate as transmitters, or as transmitters and receivers, at a given time.

It will be appreciated that, depending on the modality, the transmitting sensor may also operate as a receiving sensor. For example, an ultrasound transducer may operate both as a transmitter and receiver. Similarly, an optical-fiber end may operate as both, for example, as illustrated in conjunction with FIG. 10B, hereinbelow. Yet, for x-ray CT, dedicated transmitters and receivers may be used.

Figure 6C:
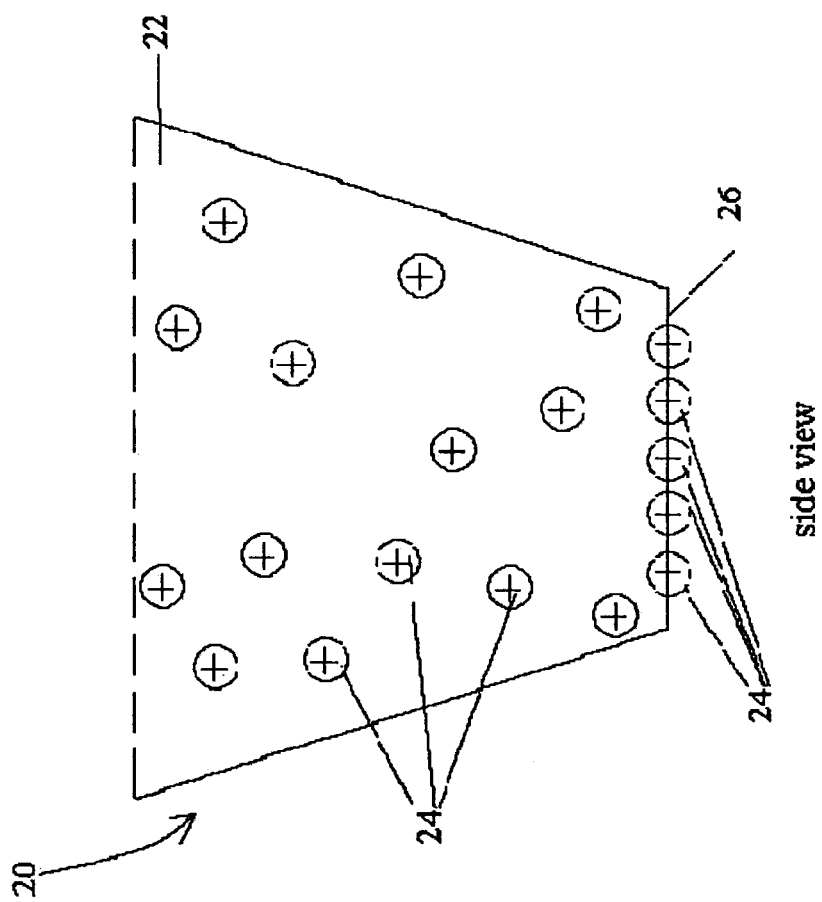

As seen in FIG. 6C, the sensors 24 may be randomly spread, and any one sensor 24 may operate as a transmitting sensor, or as a transmitting and receiving sensor, at any one time. The associated algorithm provides the three-dimensional information, for the specific arrangement.

FIGS. 6D-6F illustrate configurations that may be used to provide a three dimensional image of a tissue voxel of the tissue 44.

As seen in FIG. 6D, the sensor 24 has a viewing angle $\beta$.

As seen in FIG. 6E, when several sensors 24, such as sensor 24D, 24E, and 24F, are arranged along the element 20, formed as a flat plate:
the tissue voxel 44x is not viewed by any of the sensors;
the tissue voxel 44i is viewed only by the sensor 24D;
the tissue voxel 44j is viewed by both the sensors 24D and 24E; and
the tissue voxel 44k is viewed by the three sensors 24D, 24E and 24F.

As illustrated, some three dimensional information may be obtained for the voxels 44j and 44k.

Alternatively, as seen in FIG. 6F, when several sensors 24, such as sensor 24G, 24H, 24I, and 24J, are arranged along the element 20, formed as a cone or a cylinder:
the tissue voxel 44u is viewed by all the four sensors, 24G, 24H, 24I, and 24J;
the tissue voxel 44v is viewed by the three sensors, 24G, 24H, and 24J; and
the tissue voxel 44w is viewed by the two sensors, 24I and 24J.

Thus, in the configuration of FIG. 6F, some three dimensional information may be obtained for all the tissue voxels.

Naturally, a shape with a curvature, such as a circular or elliptical arrangement or a section thereof is preferred to the flat plate arrangement. Nonetheless, the flat plate arrangement does yield some three-dimensional information, and is within the scope of the present invention.

It will be appreciated that, while effective contact is highly desirable, the three-dimensional information may be achieved also without effective contact, thus without the mechanism for applying the force to the tissue, with the line of force at the acute angle $\alpha$ to the linear rigid surface 22, as described in conjunction with FIGS. 1A-1V. Hence shapes that do not meet this criterion may nonetheless be used for the small-scale computerized tomography.

While the shapes illustrated in FIGS. 1O, 1P, 1Q, 1S, 1T, and 1U are the most preferred, since they provide both effective contact and curvature, other shapes may also be used, as illustrated in FIGS. 6G-6N.

FIGS. 6G-6M schematically illustrate elements 20A, shaped with a curvature, which may be round, oval, or of another shape, for providing the three-dimensional information, but without necessarily providing the effective contact.

These may include a cylinder (FIGS. 6G and 6K), a half an egg-like shape (FIGS. 6H and 6L), a semi sphere (FIG. 6J), and a barrel shape (FIGS. 6I and 6M). It will be appreciated that many other shapes are also possible.

A curvature may be defined, vis a vis FIG. 6N, as the ratio of an average change in the angles $\delta(1), \delta(2), \delta(3), \ldots$ of a tangent that moves over a given arc 20B to the length of the arc t.

Preferably, the curvature of the element 20A is at least greater than that of a circle having a diameter of 8 cm. Moreover, the curvature of the element 20A may be at least greater than that of a circle having a diameter of 6 cm. Furthermore, the curvature of the element 20A may be at least greater than that of a circle having a diameter of 4 cm. Additionally, the curvature of the element 20A may be at least greater than that of a circle having a diameter of 2 cm. Moreover, the curvature of the element 20A may be at least greater than that of a circle having a diameter of 1 cm. Furthermore, the curvature of the element 20A may be at least greater than that of a circle having a diameter of 0.8 cm. Greater curvatures still may also be possible.

The sensors of FIGS. 6A-6N for providing three-dimensional information may be irradiative sensors, such as optical sensors, X-ray sensors, RF sensors, MW sensors, infrared thermography sensors, and ultrasound sensors. Additionally, or alternatively, the sensors may be mechanical sensors, MR sensors, impedance sensors, nonirradiative RF sensors, radioactive-emission sensors arranged for SPECT, radioactive-emission sensors arranged for PET, and (or) other tissue characterization sensors, as known. It will be appreciated that other sensors may be used, for example, biosensors or chemical sensors, for providing surface information at different points along the tissue 44, without providing volumetric three-dimensional information.

FIG. 6-O is a flowchart illustrating a method 130 of tissue characterization, with small-scale computerized tomography, for obtaining three-dimensional information of a volumetric region of the tissue, in accordance with some embodiments of the present invention. The method 130 includes:

in a box 132: arranging at least two sensors for tissue characterization on a curved surface, so that the at least two sensors view a same volumetric region of the tissue;

in a box 134: performing measurements with the at least two sensors; and in a box 136: analyzing the measurements to obtain the three-dimensional information of the volumetric region.

Referring further to the drawings, FIGS. 7A-7C schematically illustrate a device 100 for effective contact, in accordance with an embodiment of the present invention. FIGS. 7A-7C are based on a method taught by commonly owned U.S. patent application Ser. No. 11/196,732, filed on Aug. 4, 2005, whose disclosure is incorporated herein by reference. Yet, as described here, the device 100 has a substantially conical structure 125, configured for making contact with the tissue. It will be appreciated that the device may be elliptical or circular in cross section. The conical structure 125 may be, for example, as described in FIG. 1O, transversely, and in FIG. 1S, longitudinally.

The conical structure 125 defines an effective diameter 123 in a first direction and a longitudinal axis 121 in a second direction. Thus, the conical structure 125 is curved in the first direction and has a linear cross section in the second direction.

The device 100 operates by two mechanisms, as follows:

a mechanism, which exerts a force F on the tissue 44, in the second direction, along the longitudinal axis 121, for fixing the tissue 44 against the device 100, so as to substantially immobilize the tissue 44; and a counter mechanism, which presses the at least one piston sensor 24, associated with it, against the immobilized tissue 44, by exerting a counter force $F_c$, in opposition to at least a component of the force F, thus achieving effective contact between the surface 44 and the at least one piston sensor 24.

As a first step, seen in FIGS. 7A-7B, the mechanism for the force F is provided by a vacuum line 116, for creating suction in the conical structure 125 (FIG. 7A), thus sucking the tissue 44 towards the rigid surface 22 of the conical cross section (FIG. 7B).

The longitudinal axis 121 defines a line of force for the force F, at the acute angle λ to the rigid surface 22 of the linear cross section, the linear cross section being in the direction of the line of force (the second direction).

As a second step, seen in FIG. 7C, the counter mechanism, for the counter force $F_c$ in opposition to the force F, is provided by the piston 120, moving in the direction of an arrow 120, and pressing the at least one piston sensor 24 into the immobilized tissue 44, thus achieving affective contact between the at least one piston sensor 24 and the portion of the immobilized tissue 44 in contact with the at least one piston sensor 24.

Seals 115 between the piston 120 and the inner walls 122 of the device 100 ensure the vacuum in the vacuum line 116.

It will be further appreciated that one or several cone sensors 24M may be mounted on the rigid surface 22, arranged so as to provide three dimensional information of the tissue 44.

Thus, the cone sensors 24M will enjoy the effective contact formed by the force F at the acute angle λ to the rigid surface 22 of the linear cross section (FIG. 7A), for stretching or stretching and pushing the tissue 44 against the rigid surface 22. Yet, the cone sensors 24M will not benefit from the second mechanism, of the piston 120, which pushes the at least one piston sensor 24 against the tissue 44, with the force $F_c$, seen in FIG. 7C.

The at least one piston sensor 24 and the at least one cone sensor 24M may be optical sensors, X-ray sensors, RF sensors, MW sensors, infrared thermography sensors, ultrasound sensors, MR sensors, impedance sensors, temperature sensors, biosensors, chemical sensors, radioactive-emission sensors, mechanical sensors, nonirradiative RF sensors, or any other tissue characterization sensor, as known.

Figure 7D:
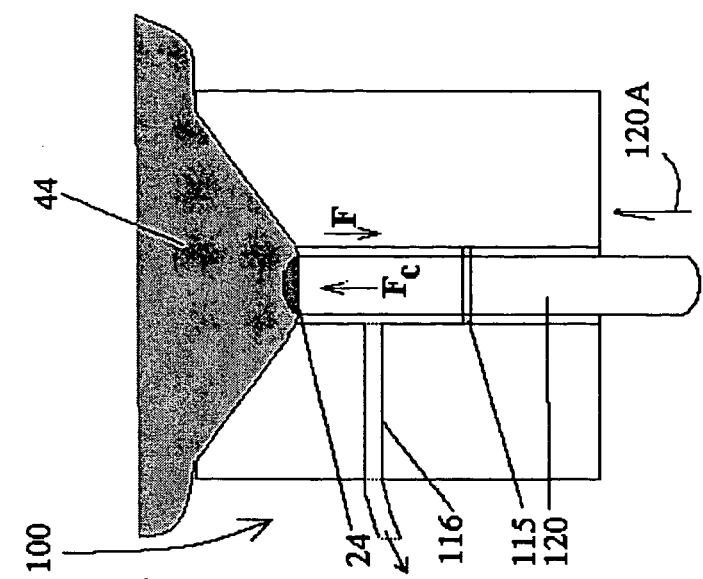
FIGS. 7D-7F schematically illustrate another configuration for effective contact, in accordance with another embodiment of the present invention.
Figure 7E:
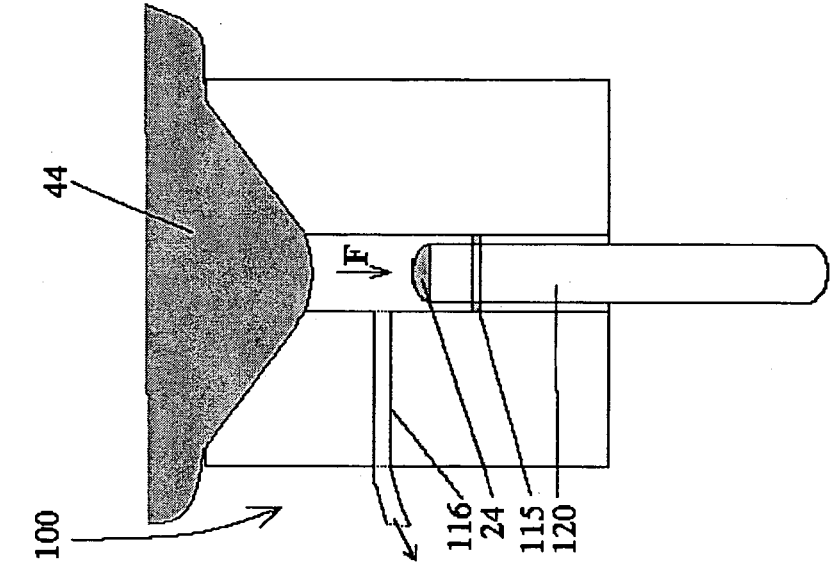
Figure 7F:
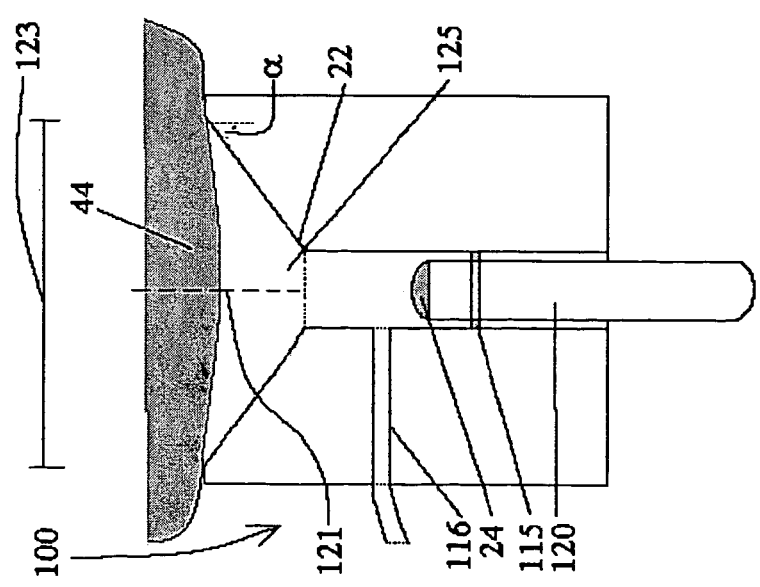

Referring further to the drawings, FIGS. 7D-7F schematically illustrate another configuration for effective contact, in accordance with another embodiment of the present invention, wherein a sensor 24 is located on the piston 120, but no cone sensors 24M are used.

Again, the line of force for the force F is at the acute angle α to the rigid surface 22 of the linear cross section of the conical structure 125, fixing the tissue 44 to the rigid surface 22.

As a second step, seen in FIG. 7F, the counter mechanism, for the counter force $F_c$ in opposition to the force F, is provided by the piston 120, moving in a direction of an arrow 120A, and pressing the at least one piston sensor 24 into the immobilized tissue 44, achieving affective contact between the piston sensor 24 and the portion of the immobilized tissue 44 in contact with the piston sensor 24.

Figure 7H:
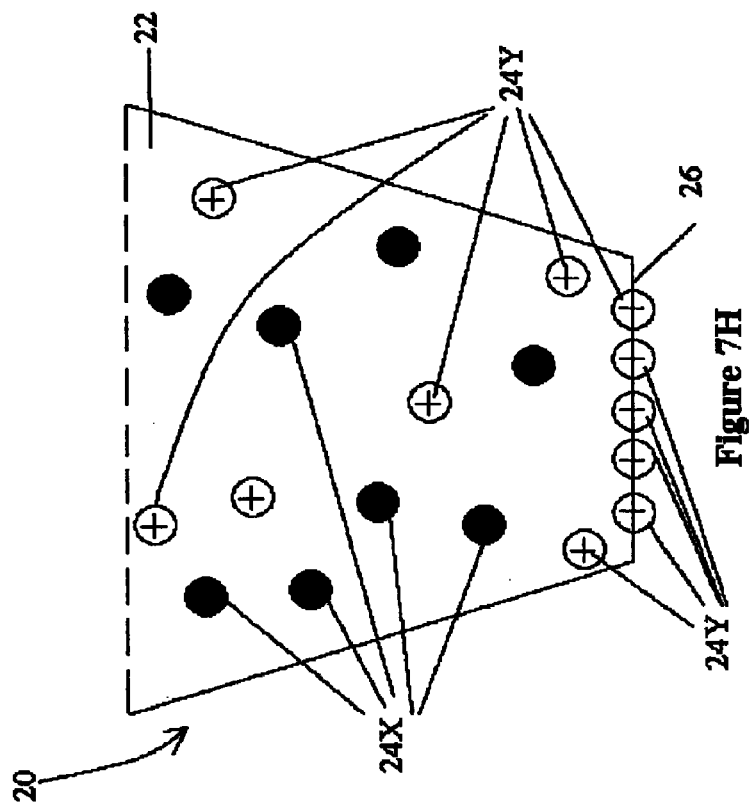
FIGS. 7G-7H schematically illustrate configurations with several types of sensors, in accordance with embodiments of the present invention.
Figure 7G:
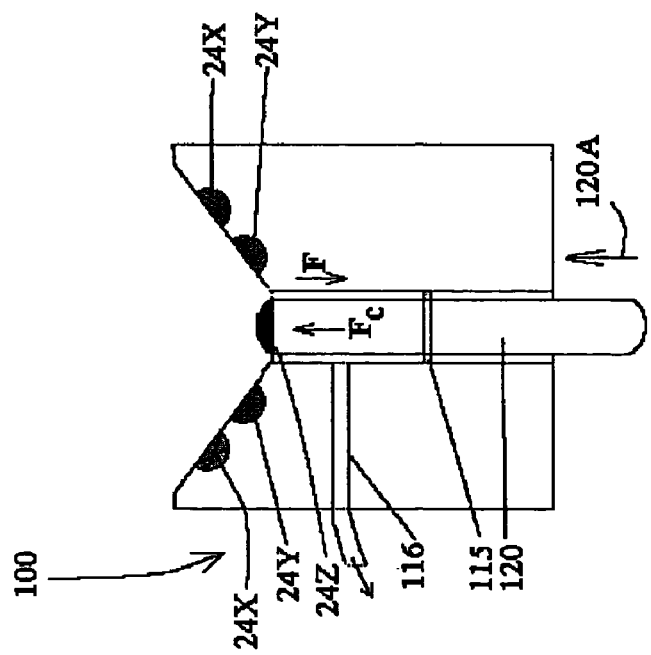

FIGS. 7G-7H schematically illustrate configurations with several types of sensors, in accordance with embodiments of the present invention.

As seen in FIG. 7G, three types of sensors may be used, cone sensors 24X and 24Y along the conical structure 125, and a piston sensor 24Z on the piston 120. This arrangement will provide three-dimensional information by both the cone sensor types 24X and 24Y. In this manner, three-dimensional information for example, by ultrasound and optical sensors, or by MRI and X-ray may obtained and compared. It will be appreciated that many combinations of mixed sensor types are possible.

It will be noted that the piston sensor 24Z is arranged so as not to provide three-dimensional information.

As seen in FIG. 7H, two types of sensors are used, 24X and 24Y, scattered on the rigid surface 22. This arrangement will again provide three-dimensional information by the sensors 24X and 24Y. Again, three-dimensional information of different modalities may be obtained and compared.

The sensors 24X, 24Y, and 24Z may be, for example, irradiative sensors, such as optical sensors, X-ray sensors, RF sensors, MW sensors, infrared thermography sensors, ultrasound sensors, or nonirradiative sensors, such as MR sensors, impedance sensors, temperature sensors, biosensors, chemical sensors, radioactive-emission sensors, mechanical sensors, nonirradiative RF sensors, or other sensors as known.

Figure 8:
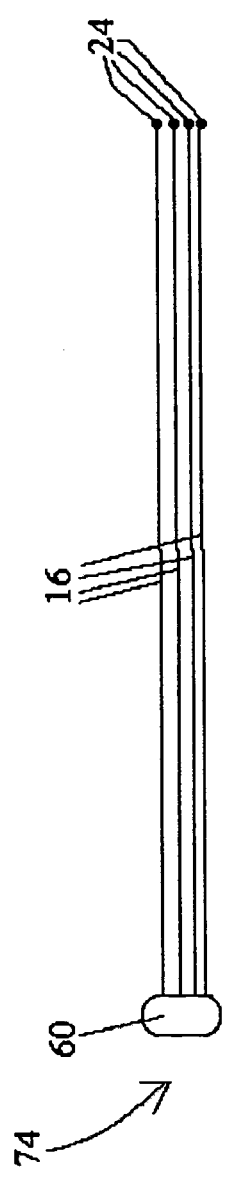
FIG. 8 schematically illustrates a first sensor construction, in accordance with some embodiments of the present invention.

FIG. 8 schematically illustrates a first sensor construction 74 for the device 10, in accordance with some embodiments of the present invention. The first sensor construction 74 is applicable to sensors 24, wherein each is operative as both a transmitter and a receiver.

Alternatively, the first sensor construction 74 is applicable to sensors 24, operative as receivers of natural signals, for example, body temperature sensors, where no transmission is necessary.

Accordingly, the first sensor construction 4 includes the signal generator and analyzer 60, the signal communication line 16 to each sensor, and the sensors 24, each operative as a transmitter and a receiver.

Figure 9:
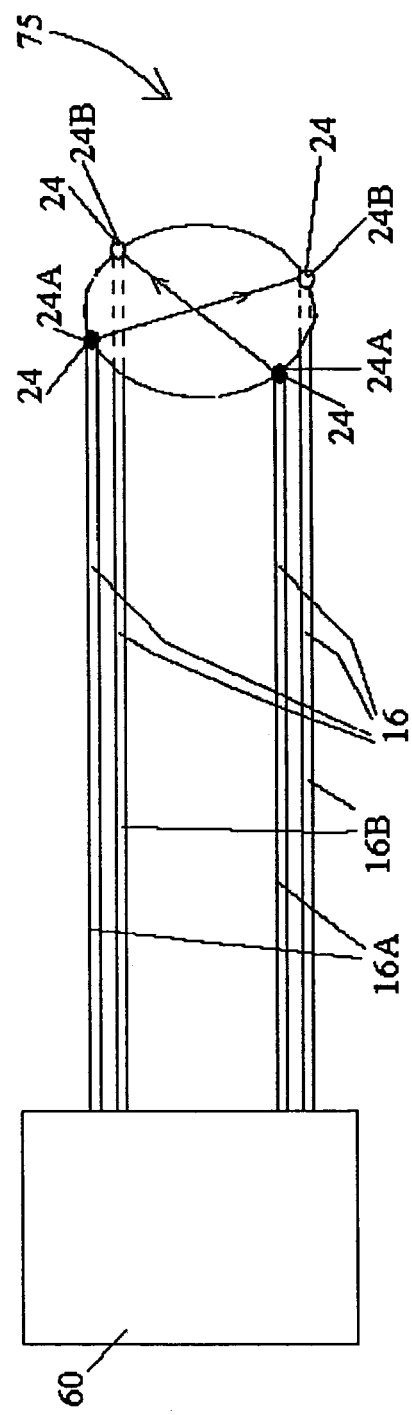
FIG. 9 schematically illustrates a second sensor construction for transmission sensing, in accordance with some embodiments of the present invention.

FIG. 9 schematically illustrates a second sensor construction 75, for the device 10, where a sensor 24A is a transmitter and a sensor 24B is a receiver, in accordance with some embodiments of the present invention. Accordingly, the second sensor construction 75 includes the signal generator and analyzer 60, signal communication lines 16A to each transmitting sensor 24A, and receiving lines 16B, from each receiving sensor 24B.

FIGS. 10A and 10B schematically illustrate optical sensor constructions for the device 10, in accordance with some embodiments of the present invention.

In accordance with one embodiment, seen in FIG. 10A, an optical sensor construction 76 includes optical signal generators 60A, such as lasers or LEDs, and optical signal analyzers 60B, formed, for example, as CCDs. The signal communication lines 16 include optical fibers 16A leading from the optical signal generators 60A to the tissue and optical fibers 16B, leading from the tissue to the optical signal analyzers 60B. The sensors 24 are the proximal endings of the optical fibers 16A and 16B, with respect to the tissue.

In accordance with another embodiment, seen in FIG. 10B, an optical sensor construction 78 includes the optical signal generators 60A, such as the lasers or the LEDs, and the optical signal analyzers 60B, for example, formed as the CCDs. The signal communication lines 16 include optical fibers leading both from the optical signal generators 60A to the tissue and from the tissue to the optical signal analyzers 60B. Beam splitters 60C, at the distal end with respect to the tissue, direct the beam from the optical signal generators 60A to the optical fibers 16 and from the optical fibers 16 to the optical signal analyzers 60B. The sensors 24 are the proximal endings of the optical fibers 16, with respect to the tissue. Other techniques for using a single optical fiber both for transmitting and for receiving optical signals may also be used.

It will be appreciated that another signal communication architecture may be used, as known.

In accordance with some embodiments of the present invention, tissue characterization may be performed by various techniques, including any one from the following nonexhaustive list.

Tissue characterization by ultrasonography: Ultrasonography is a medical imaging technique, using high frequency sound waves in the range of about 1 to 40 MHz and their echoes. The sound waves travel in the body and are reflected by interfaces between different types of tissues, such as between a healthy tissue and a denser, cancerous tissue, or between a portion of a soft tissue and a bone. The ultrasound probe receives the reflected sound waves and the associated instrumentation calculates the distances from the probe to the reflecting boundaries.

The ultrasound probe includes a piezoelectric crystal, which produces an electric signal in response to a pressure pulse. The shape of the probe determines its field of view, and the frequency of the emitted sound determines the minimal detectable object size. Generally, the probes are designed to move across the surface of the body. However, some probes are designed to be inserted through body lumens, such as the vagina or the rectum, so as to get closer to the organ being examined.

Before the early 1970's ultrasound imaging systems were able to record only the strong echoes arising from the outlines of an organ, but not the low-level echoes of the internal structure. In 1972 a refined imaging mode was introduced called gray-scale display, in which the internal texture of many organs became visible. In consequence, ultrasound imaging became a useful tool for imaging tumors, for example, in the liver.

A development of recent years is a 3D ultrasound imaging, in which several two-dimensional images are acquired by moving the probes across the body surface or by rotating probes, inserted into body lumens. The two-dimensional scans are then combined by specialized computer software to form 3D images.

In multiple-element probes, each element has a dedicated electric circuit, so that the beam can be "steered" by changing the timing in which each element sends out a pulse. By sequentially stimulating each element, the beams can be rapidly steered from the left to right, to produce a two-dimensional cross-sectional image. Additionally, transducer-pulse controls allow the operator to set and change the frequency and duration of the ultrasound pulses, as well as the scan mode of the machine. A probe formed of array transducers has the ability to be steered as well as focused.

Contrast agents may be used in conjunction with ultrasound imaging, for example as taught by U.S. Pat. No. 6,280,704, to Schutt, et al., entitled, "Ultrasonic Imaging System Utilizing a Long-Persistence Contrast Agent," whose disclosure is incorporated herein by reference.

Tissue characterization by its dielectric properties: There are several known techniques for local tissue characterization by the tissue's electromagnetic properties.

Commonly owned U.S. Pat. No. 6,813,515, to Hashimshony, entitled, "Method and System for Examining Tissue According to the Dielectric Properties Thereof," whose disclosure is incorporated herein by reference, describes a method and system for examining tissue in order to differentiate it from other tissue, according to the dielectric properties of the examined tissue. The method includes applying an electrical pulse to the tissue to be examined via a probe formed with an open cavity such that the probe generates an electrical fringe field in examined tissue within the cavity and produces a reflected electrical pulse therefrom with negligible radiation penetrating into other tissues or biological bodies near the examined tissue; detecting the reflected electrical pulse; and comparing electrical characteristics of the reflected electrical pulse with respect to the applied electrical pulse to provide an indication of the dielectric properties of the examined tissue.

Furthermore, commonly owned U.S. Patent Application 60/641,081, entitled, "Device and Method for Tissue Characterization in a Body Lumen, by an Endoscopic Electromagnetic Probe," whose disclosure is incorporated herein by reference, discloses a device and method for tissue characterization in a body lumen, for the detection of abnormalities, using an electromagnetic probe mounted on an endoscope. The endoscope may be designed for insertion in a body lumen, selected from the group consisting of an oral cavity, a gastrointestinal tract, a rectum, a colon, bronchi, a vagina, a cervix, a urinary tract, and blood vessels. Additionally, it may be designed for insertion in a trocar valve.

Additionally, commonly owned U.S. Patent Application 60/665,842, entitled, "Electromagnetic Sensors for Tissue Characterization," whose disclosure is incorporated herein by reference, discloses a sensor comprising: a resonating element, formed as a conductive structure, configured to be placed proximally to an edge of a tissue for characterization, without penetrating the tissue. The resonating element has a diameter-equivalent D, which defines a cross-sectional area thereof, on a plane substantially parallel with the edge, and at least one conductive lead, for providing communication with an external system, wherein the resonating element is configured to resonate at a free-air wavelength range of between about $\lambda$ and about $10\lambda$, wherein $\lambda$ is at least about ten times the diameter-equivalent D. Upon receiving a signal in the range of between about $\lambda$ and about $10\lambda$, the sensor is configured to induce electric and magnetic fields, in a near zone, in the tissue, the near zone being a hemisphere having a diameter of substantially D, beginning with the edge, while causing negligible radiation in a far zone, so that the tissue, in the near zone, effectively functions as part of the resonating element, varying a resonating response to the sensor, and so the tissue, in the near zone, is thereby characterized by its electromagnetic properties, by the resonating response to the sensor.

Tissue characterization by electrical impedance imaging: Electrical impedance imaging relates to measuring the impedance between a point on the surface of the skin and some reference point on the body of a patient. Sometimes, a multi-element probe, formed as a sheet having an array of electrical contacts, is used for obtaining a two-dimensional impedance map of the tissue, for example, the breast. The two-dimensional impedance map may be used, possibly in conjunction with other data, such as mammography, for the detection of cancer.

Rajshekhar, V. ("Continuous Impedance Monitoring During CT-Guided Stereotactic Surgery: Relative Value in Cystic and Solid Lesions," Rajshekhar, V., British Journal of Neurosurgery, 1992, 6, 439-444) describes using an impedance probe with a single electrode to measure the impedance characteristics of lesions. The objective of the study was to use the measurements made in the lesions to determine the extent of the lesions and to localize the lesions more accurately. The probe was guided to the tumor by CT and four measurements were made within the lesion as the probe passed through the lesion. A biopsy of the lesion was performed using the outer sheath of the probe as a guide to position, after the probe itself was withdrawn.

U.S. Pat. No. 4,458,694, to Sollish, et al., entitled, "Apparatus and Method for Detection of Tumors in Tissue," whose disclosure is incorporated herein by reference, relates to an apparatus for detecting tumors in human breast, based on the dielectric constants of localized regions of the breast tissue. The apparatus includes a probe, including a plurality of elements. The apparatus further includes means for applying an AC signal to the tissue, means for sensing dielectric properties at each of the probe elements at different times, and signal processing circuitry, coupled to the sensing means, for comparing the dielectric properties sensed at the different times. The apparatus thus provides an output of the dielectric constants of localized regions of breast tissue associated with the probe.

Similarly, U.S. Pat. No. 4,291,708 to Frei, et al., entitled, "Apparatus and Method for Detection of Tumors in Tissue," whose disclosure is incorporated herein by reference, relates to apparatus for detecting tumors in human breast tissue, by the dielectric constants of a plurality of localized regions of human breast tissue.

U.S. Pat. Nos. 6,308,097; 6,055,452; and 5,810,742, to Pearlman, A. L., entitled, "Tissue Characterization Based on Impedance Images and on Impedance Measurements," whose disclosures are incorporated herein by reference, describe apparatus for aiding in the identification of tissue type for an anomalous tissue in an impedance image. The device comprises: means for providing a polychromic emmitance map of a portion of the body; means for determining a plurality of polychromic measures from one or more portions of the body; and a display of an indication based on the plurality of polychromic measures.

Tissue characterization by optical fluorescence spectroscopy: When a sample of large molecules is irradiated, for example, by laser light, it will absorb radiation, and various levels will be excited. Some of the excited states will revert back substantially to the previous state, by elastic scattering, and some energy will be lost in internal conversion, collisions and other loss mechanisms. However, some excited states will create fluorescent radiation, which, due to the distribution of states, will give a characteristic wavelength distribution.

Some tumor-marking agents give well-structured fluorescence spectra, when irradiated by laser light. In particular, hematoporphyrin derivatives (HPD), give a well-structured fluorescence spectrum, when excited in the Soret band around 405 nm. The fluorescence spectrum shows typical peaks at about 630 and 690 nm, superimposed in practice on more unstructured tissue autofluorescence. Other useful tumor-marking agents are dihematoporphyrin ether/ester (DHE), hematoporphyrin (HP), polyhematoporphyrin ester (PHE), and tetrasulfonated phthalocyanine (TSPC), when irradiated at 337 nm ($N_2$ laser).

U.S. Pat. No. 5,115,137, to Andersson-Engels, et al., entitled, "Diagnosis by Means of Fluorescent Light Emission from Tissue," whose disclosure is incorporated herein by reference, relates to improved detection of properties of tissue by means of induced fluorescence of large molecules. The tissue character may then be evaluated from the observed large-molecule spectra. According to U.S. Pat. No. 5,115,137, the spectrum for tonsil cancer is clearly different from that of normal mucosa, due to endogenous porphyrins.

U.S. Pat. No. 6,258,576, to Richards-Kortum, et al., entitled, "Diagnostic Method and Apparatus for Cervical Squamous Intraepithelial Lesions In Vitro and In Vivo Using Fluorescence Spectroscopy," whose disclosure is incorporated herein by reference, relates to the use of multiple illumination wavelengths in fluorescence spectroscopy for the diagnosis of cancer and precancer, for example, in the cervix. In this manner, it has been possible to (i) differentiate normal or inflamed tissue from squamous intraepithelial lesions (SILs) and to (ii) differentiate high grade SILs from non-high grade SILs. The detection may be performed in vitro or in vivo. Multivariate statistical analysis has been employed to reduce the number of fluorescence excitation-emission wavelength pairs needed to re-develop algorithms that demonstrate a minimum decrease in classification accuracy. For example, the method of the aforementioned patent may comprise illuminating a tissue sample with electromagnetic radiation wavelengths of about 337 nm, 380 nm and 460 nm, to produce fluorescence; detecting a plurality of discrete emission wavelengths from the fluorescence; and calculating from the emission wavelengths a probability that the tissue sample belongs in particular tissue classification.

Commonly owned U.S. Patent Application 2003/0138378, to Hashimshony, entitled, "Method and Apparatus for Examining Tissue for Predefined Target Cells, Particularly Cancerous Cells, and a Probe Useful for Such Method and Apparatus," whose disclosure is incorporated herein by reference, teaches a method, apparatus, and probe for examining tissue and characterizing its type according to measured changes in optical characteristics of the examined tissue. In a preferred embodiment of this method the tissue to be examined is subject to a contrast agent containing small particles of a physical element conjugated with a biological carrier selectively bindable to the target cells. Additionally, energy pulses are applied to the examined tissue, and the changes in impedance and/or the optical characteristics produced by the applied energy pulses are detected and utilized for determining the presence of the target cells in the examined tissue. Furthermore, in a preferred embodiment, the applied energy pulses include laser pulses, and the physical element conjugated with a biological carrier is a light-sensitive semiconductor having an impedance which substantially decreases in the presence of light. Moreover, the same probe used for detecting the targeted cells, may also be used for destroying the cells so targeted.

Tissue characterization by optical reflectance spectroscopy: The application optical reflectance spectroscopy for tissue characterization is described, for example, in www.sbsp-limb.nichd.nih.gov/html/spectroscopy.html, downloaded on Mar. 15, 2005, disclosing an optical reflectance spectroscopy (ORS) device for measuring the thickness of the epithelial layer, and an evaluation technique based on oblique angle reflectance spectroscopy, that allows assessment of the scattering and absorption properties of the epithelium and stroma, thus providing information on chronic oral epithelial tissue inflammation, which is considered a potential diagnostic precursor to oral cancer.

Additionally, Tomatis, A., et al., studied reflectance images of 43 pigmented lesions of the skin (18 melanomas, 17 common melanocytic naevi and eight dysplastic naevi). Reflectance images were acquired by a telespectrophotometric system and were analyzed in the spectral range from 420 to 1040 nm, to discriminate melanoma from benign melanocytic entities. Different evaluations were carried out considering the whole spectrum, the visible and the near infrared. A total of 33 (76.7%) lesions were correctly diagnosed by the telespectrophotometric system, compared with 35 (81.4%) correct clinical diagnoses. Reflectance in the infrared band appears diagnostically relevant.

Tissue characterization by magnetic resonance (MR): Magnetic resonance is based on the absorption and emission of energy in the radio frequency range of the electromagnetic spectrum, by nuclei having unpaired spins. Magnetic Resonance Imaging (MRI) is based on the imaging of the absorption and emission of energy in the radio frequency range of the electromagnetic spectrum, by nuclei having unpaired spins.

Conventional MRI utilizes a large-apparatus, for whole body imaging, having:

i. a primary magnet, which produces the $B_o$ field for the imaging procedure;

ii. gradient coils for producing a gradient in $B_o$;

iii. an RF coil, for producing the $B_1$, magnetic field, necessary to rotate the spins by 90° or 180° and for detecting the MR signal; and iv. a computer, for controlling the components of the MR imager.

Generally, the magnet is a large horizontal bore superconducting magnet, which provides a homogeneous magnetic field in an internal region within the magnet. A patient or object to be imaged is usually positioned in the homogeneous field region located in the central air gap for imaging. A typical gradient coil system comprises an anti-Helmholtz type of coil. These are two parallel ring-shaped coils, around the z axis. Current in each of the two coils flows in opposite directions creating a magnetic field gradient between the two coils.

The RF coil creates a $B_1$, field, which rotates the net magnetization in a pulse sequence. The RF coils may be: 1) transmit and receive coils, 2) receive only coils, or 3) transmit only coils.

As described hereinabove, the MRI relies on a magnetic field in an internal region within the magnet. As such, it is unsuitable as a handheld probe or an endoscopic probe, because the tissue to be imaged has to be in the internal region of the imager.

However, U.S. Pat. No. 5,572,132, to Pulyer, et al., entitled, "MRI Probe for External Imaging," whose disclosure is incorporated herein by reference, describes an MRI spectroscopic probe having an external background magnetic field $B_0$ (as opposed to the internal background magnetic field of the large horizontal bore superconducting magnet). Thus, an MRI catheter for endoscopical imaging of tissue of the artery wall, rectum, urinal tract, intestine, esophagus, nasal passages, vagina and other biomedical applications may be constructed. The probe comprises (i) a miniature primary magnet having a longitudinal axis and an external surface extending in the axial direction, and (ii) an RF coil surrounding and proximal to the surface. The primary magnet is structured and configured to provide a symmetrical, preferably cylindrically shaped, homogeneous field region external to the surface of the magnet. The RF coil receives NMR signals from excited nuclei. For imaging, one or more gradient coils are provided to spatially encode the nuclear spins of nuclei excited by an RF coil, which may be the same coil used for receiving NMR signals or another RF coil.

Additionally, commonly owned U.S. Patent Application 2005/0021019 to Hashimshony, et al., entitled "Method and Apparatus for Examining Substance, Particularly Tissue, to Characterize its Type," whose disclosure is incorporated herein by reference, describes a method and apparatus for examining a substance volume to characterize its type, by: applying a polarizing magnetic field through the examined substance; applying RF pulses locally to the examined substance volume such as to invoke electrical impedance (EI) response signals corresponding to the electrical impedance of the substance, and magnetic resonance (MR) response signals corresponding to the MR properties of the substance; detecting the EI and MR response signals; and utilizing the detected response signals for characterizing the examined substance volume type.

Contrast agents may be used in conjunction with MRI. For example, U.S. Pat. No. 6,315,981 to Unger, entitled, "Gas Filled Microspheres as Magnetic Resonance Imaging Contrast Agents," whose disclosure is incorporated herein by reference, describes the use of gas filled microspheres as contrast agents for MRI.

Additionally, U.S. Pat. No. 6,747,454, to Belt, entitled, "Array of Coils for Use in Imaging the Vasculature of a Patient," whose disclosure is incorporated herein by reference, describes an array of coils, configured for use in imaging the vasculature of a patient.

Furthermore, U.S. Pat. No. 6,677,755, to Belt, et al., "Circuit for Selectively Enabling and Disabling Coils of a Multi-Coil Array," whose disclosure is incorporated herein by reference, describes a circuit, used to selectively enable and disable n-coils. The circuit includes n-drivers powered by a current source. Each n-driver includes a pair of FETs disposed such that a gate of one FET is connected to a gate of the other FET to form a common gate node thereat. The n-drivers are disposed in a totem-pole configuration. The first FET of a first of the n-drivers has (A) a drain linked to a ground and to an end of a first of the n-coils and (B) a source linked to a drain of the first FET of a second of the n-drivers and to an end of a second of the n-coils. The other FET of the first of the n-drivers has (A) a source linked to an opposite end of the first of the n-coils and (B) a drain linked to the end of the second of the n-coils and to the source of the first FET of the first of the n-drivers. The first FET of the second of the n-drivers also has a source linked to a drain of the first FET of a successive n-driver and to an end of a successive n-coil. The other FET of the second of the n-drivers also has (A) a source linked to an opposite end of the second of the n-coils and (B) a drain linked to the end of the successive n-coil and to the source of the first FET of the second of the n-drivers. This continues until the first FET and the other FET of an nth of the n-drivers are likewise disposed in the totem-pole configuration of the n-drivers, with a source and a drain of the first FET and the other FET, respectively, of the nth of the n-drivers being connected to the current source. Each of the n-drivers is used to operate a corresponding one of the n-coils by being responsive at its common gate node (i) to a coil disable signal by activating the first FET thereof and deactivating the other FET thereof thereby not only drawing current away from and thus disabling the corresponding coil but also allowing the current to flow through the first FET and thus to be available as a source of current to a successive one of the n-drivers and (ii) to a coil enable signal by deactivating the first FET thereof and activating the other FET thereof thereby allowing the current not only to flow serially through the corresponding coil and the other FET thus enabling the corresponding coil but also to be available as a source of current to the successive one of the n-drivers.

Tissue characterization by magnetic resonance spectroscopy (MRS): In MRS, spectroscopic NMR data is obtained from the examined area. Thus the biochemical information obtained from MRS can be interpreted in relation to a defined anatomical location, and images of metabolite distributions can be generated. MRS can be used to identify surrogate biochemical markers of cellular transformation, thus differentiating benign tumors from malignant ones, and identifying different tumor types. Prognostic and diagnostic information is derived from the spectrum of malignant tumors (Breast Cancer Res. 2001, 3:36-40).

Tissue characterization by radioactive emission: Radioactive-emission imaging relies on the fact that, in general, pathologies, such as malignant tumors and inflammations, display a level of activity different from that of healthy tissue. Thus, radiopharmaceuticals, which circulate in the blood stream, are picked up by the active pathologies to a different extent than by the surrounding healthy tissue; in consequence, the pathologies are operative as radioactive-emission sources and may be detected by radioactive-emission imaging.

The pathological feature may appear as a concentrated source of high radiation, or a hot region, as may be associated with a tumor, or as a region of low-level radiation, which is nonetheless above the background level, as may be associated with carcinoma. Additionally, a reversed situation is possible. Dead tissue has practically no pick up of radiopharmaceuticals, and is thus operative as a region of little radiation, or a cold region, below the background level.

Thus radiopharmaceuticals may be used for identifying active pathologies as well as dead tissue, and the image that is constructed is generally termed, a "functional image."

The mechanism of localization of a radiopharmaceutical depends on various processes in the organ of interest, such as antigen-antibody reactions, physical trapping of particles, receptor site binding, removal of intentionally damaged cells from circulation, and transport of a chemical species across a cell membrane and into the cell by a normally operative metabolic process. A summary of the mechanisms of localization by radiopharmaceuticals is found in www.lunis.luc.edu/nucmed/tutorial/radpharm/i.htm.

The particular choice of a radionuclide for labeling antibodies depends upon the chemistry of the labeling procedure and the isotope nuclear properties, such as, the number of gamma rays emitted, their respective energies, the emission of other particles, such as beta or positrons, the isotope half-life, and the existence of different isotopes of identical chemistry but different half-lives (e.g., $I^{131}$ and $I^{133}$). The usual preferred emission for medical applications is that of gamma rays. However, beta and positron radiation may also be detected, and are of particular relevance in PET imaging.

The sensor may be a room temperature, solid-state CdZnTe (CZT) detector, configured as a single-pixel or a multi-pixel detector. Alternatively, another solid-state detector such as CdTe, HgI, Si, Ge, or the like, or a scintillation detector, such as NaI(Tl), LSO, GSO, CsI, CaF, or the like, or a combination of scintillation materials and photodiode arrays may be used.

Two technologies of computed tomography for radioactive emission are known.

i. Single photon emission computed tomography (SPECT), in which single radioactive emission events are detected around a body. The detection of a large number of photons may be used to form a three-dimensional functional image and thus identify the source of the radiation.

ii. Positron emission tomography (PET), in which a positron is emitted from the radioactive isotope. Upon its interaction with an electron, annihilation occurs, and the two photons produced by the annihilation travel in opposite directions. Their detection by coincidence counting identifies an exact path upon which the annihilation took place. Again, the detection of a large number of photons may be used to form a three-dimensional functional image and identify the source of the radiation, especially using the fact that in PET, the photon paths for coincidence counts are known, Attenuation by the surrounding tissue introduces a certain error.

Various radiopharmaceuticals can be synthesized to target specific molecules present in the target tissue cells, for example, $[^{18}F]$ FDG (fluorodeoxyglucose), or antibody fragment labeled with $[^{64}Cu]$. Others may be found in www.crump.ucla.edu/software/lpp/radioisotopes/tracers.html. Additional details and descriptions may be found in Breast Cancer Res. 2001, 3:28-35.

Tissue characterization by temperature imaging: Temperature imaging for locating and detecting neoplastic tissue has been known since the 1950's, when it was discovered that the surface temperature of skin in the area of a malignant tumor exhibited a higher temperature than that expected of healthy tissue. Thus, by measuring body skin temperatures, it became possible to screen for the existence of abnormal body activity such as cancerous tumor growth. With the development of liquid crystals and methods of forming temperature responsive chemical substrates, contact thermometry became a reality along with its use in medical applications. Devices employing contact thermometry could sense and display temperature changes through indicators which changed colors, either permanently or temporarily, when placed in direct physical contact with a surface such as skin, reflecting a temperature at or near the point of contact. An abnormal reading would alert a user to the need for closer, more detailed examination of the region in question. However, the art in this area has been directed primarily at sensing and displaying temperatures on exterior skin surfaces.

U.S. Pat. No. 3,830,224, to Vanzetti, et al., whose disclosure is incorporated herein by reference, discloses the placement of temperature responsive, color changing liquid crystals at various points in a brassiere for the purpose of detecting the existence of breast cancer.

U.S. Pat. RE 32,000, to Sagi, entitled, "Device for Use in Early Detection of Breast Cancer," whose disclosure is incorporated herein by reference, discloses a device comprising a flexible, heat-conductive web, preferably in the form of a disc-removably secured thereto by the adhesive layer. On the other side thereof, the device comprises an array of spaced-apart indicators, each of the indicators comprising a dye or a pigment and a temperature sensitive substance (crystalline organic chemical) which melts at a relatively precise temperature which is approximately 0.5 degree. F different from the adjacent indicator. As many indicators are used as are necessary to cover the desired temperature range. The device is incorporated into the breast-receiving cups of a brassiere and mirror image quadrants of the two breasts are scanned and the device is visually examined to determine the number of indicators which have displayed a change in color, thus apprising the person of the existence of abnormality in the mammary tissue.

U.S. Pat. No. 6,135,968, to Brounstein, entitled, "Differential Temperature Measuring Device and Method", whose disclosure is incorporated herein by reference, describes a device and method for sensing temperatures at internal body locations non-surgically accessible only through body orifices. The device is particularly useful in medical applications such as screening for cancer and other abnormal biological activity signaled by an increase in temperature at a selected site. As applied to prostate examinations, the device is temporarily, adhesively affixed to a user's fingertip or to a mechanical probe. In the preferred embodiment, the device includes two temperature-sensing elements, which may include a plurality of chemical indicators. Each indicator changes color in response to detection of a predetermined particular temperature. When properly aligned and installed, the first element is located on the palmar surface of the fingertip while the second element is located on the dorsal surface of the fingertip. After an examination glove has been donned over the fingertip carrying the device, a prostate examination is performed during which the first element is brought into constant but brief contact with the prostate region and the second element is similarly, simultaneously brought into contact with a dermal surface opposing the prostate region. Upon withdrawal of the fingertip from the rectum and removal of the glove, the two temperature sensing elements may be visually examined in order to determine the temperatures detected by each one. A significant difference in observed temperatures indicates the possibility of abnormal biological activity and the need for further diagnostic or medical procedures.

Tissue characterization using biosensors: Biosensors may be of catalytic type such as integrated enzymes, cellular organelles, tissues or whole microorganisms with transducers that convert a biological response into a digital electronic signal. The principal transducers used are electrochemical, optical, or thermometric. Biosensors may also be of affinity type. Affinity biosensors deliver information about the binding of antibodies to antigens, cell receptors to their ligands, and DNA and RNA to nucleic acid with a complementary sequence. Still, additional types are fully integrated biochip devices that perform as micro bio-reactors. All types can be used in high-density arrays of bio-molecular sensors.

Some of these sensors are further discussed in:
  (i) Enzyme and Microbial Biosensors: Techniques and Protocols, A. Mulchandani & K. R. Rogers (Humana Press, 1998);
  (ii) Affinity Biosensors: Techniques and Protocols, A. Mulchandani & K. R. Rogers (Humana Press, 1998);
  (iii) Journal: Biosensors & Bioelectronics:
    a. Volume 20, Issue 8, Pages 1459-1695 (15 Feb. 2005);
    b. Volume 20, Issue 6, Pages 1029-1259 (15 Dec. 2004);
    c. Volume 20, Issue 5, Pages 917-1028 (15 Nov. 2004);
    d. Volume 20, Issue 1, Pages 1-142 (30 Jul. 2004);
    e. Volume 20, Issue 12, Pages 2387-2593 (15 Jun. 2005);
  (iv) Journal: Sensors & Actuators B (chemical).
    a. Volume 103, Issues 1-2, Pages 1-473 (29 Sep. 2004);
    b. Volume 102, Issue 1, Pages 1-177 (Sep. 2004); and
    c. Volume 106, Issue 1, Pages 1-488 (29 Apr. 2005).

Tissue characterization using chemical sensors: Chemical sensors detect the presence of various types of chemical compounds and states. These include, for example, ions, such as, but not limited to, Na, K; dissolved gases, such as, but not limited to, oxygen, carbon dioxide; and sensors for determining Ph of solution.

Some of these sensors are further discussed in:
  (i) Sensors: A Comprehensive Survey. Volume 2: Chemical and Biochemical
Sensors, Part I, W. Gopel, J. Hesse, & J. N. Zemel (VCH, 1991);
  (ii) Sensors: A Comprehensive Survey. Volume 3: Chemical and Biochemical
Sensors, Part II, W. Gopel, J. Hesse, & J. N. Zemel (VCH, 1992); and
  (iii) Journal: Sensors & Actuators B (Chemical):
    a. Volume 103, Issues 1-2, Pages 1-473 (29 Sep. 2004);
    b. Volume 102, Issue 1, Pages 1-177 (Sep. 2004);
    c. Volume 108, Issues 1-2, Pages 1-1000 (22 Jul. 2005).

Tissue characterization using mechanical sensors: Mechanical sensors measure a physical property of the tissue in contact with the sensor. One example of a mechanical sensor uses tactile sensing that measures the pressure sensed on the sensor surface. An optical tactile sensor having a transparent elastic tactile portion has been taught in U.S. Pat. No. 6,909,084 to Tachi and Kajimoto, whose disclosure is incorporated herein by reference. This is an optical tactile sensor with a tactile section and imaging means, the tactile section comprising a transparent elastic body and a plurality of groups of markers provided inside the elastic body, each marker group made up of a number of colored markers, with markers making up different marker groups having different colors for each group, and behavior of the colored markers when an object touches the elastic body being photographed by the imaging means. Preferably the marker groups have mutually different spatial arrangements. Furthermore, mechanical sensors are discussed in: Sensors: A Comprehensive Survey, Volume 7: Mechanical Sensors, W. Gopel, J. Hesse, & J. N. Zemel (VCH, 1994).

It will be appreciated that the method, in accordance with some embodiments of the present invention may adapted for human tissue and for animal tissue.

It will be appreciated that the probes according to embodiments of the present invention may be applied extracorporeally, to the skin. Alternatively, they may be applied to subcutaneous tissue, during open surgery.

It will be appreciated that the probes according to embodiments of the present invention may be insertion intracorporeally, for a minimally invasive procedure, having an incision, for example, no greater than about 3 centimeters.

Alternatively, they may be inserted to a body lumen.

It is expected that during the life of this patent many relevant broad-band sensors for tissue characterization will be developed and the scope of the term broad-band sensor for tissue characterization is intended to include all such new technologies a priori.

As used herein the term "about" and "substantially" refer to ±20%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, any citation or identification of any reference in this application shall not be construed as an admission that such reference is available as prior art to the present invention.

What is claimed is:

1. A device, comprising:
    an element, which defines a rigid surface of a linear cross-section, configured to make contact with a tissue;
    a plurality of sensors, in physical contact with the rigid surface; and
    a mechanism, adapted for applying a force to the tissue, the line of force being at an acute angle with the rigid surface, for stretching the tissue against the rigid surface, thus achieving effective contact between the tissue and the rigid surface, wherein the element defines a curvature of said rigid surface for obtaining three-dimensional information, and further wherein the plurality of sensors includes at least two sensors, arranged along the curvature of the rigid surface, each defining a viewing angle, the at least two sensors sharing a portion of their viewing angles so as to obtain three-dimensional information.

2. The device of claim 1, wherein the stretching further includes stretching and pushing.

3. The device of claim 1, wherein the acute angle is between 30 degrees and 60 degrees.

4. The device of claim 1, wherein the effective contact is a contact level of at least 95%.

5. The device of claim 1, wherein the effective contact is a contact level of at least 99%.

6. The device of claim 1, wherein the effective contact is a contact level of at least 99.5%.

7. The device of claim 1, wherein the effective contact is a contact level of at least 99.8%.

8. The device of claim 1, wherein at least one of the plurality of sensors is an irradiative sensor of a wavelength $\lambda$, and an average distance t1, between external-most surfaces of the tissue and the sensor, is such that $t1 < \lambda/3$.

9. The device of claim 1, wherein at least one of the plurality of sensors is an irradiative sensor of a wavelength $\lambda$, and an average distance t1 between external-most surfaces of the tissue and the sensor is such that $t1 < \lambda/10$.

10. The device of claim 1, wherein at least one of the plurality of sensors is an irradiative sensor of a wavelength $\lambda$, and an average distance t1, between external-most surfaces of the tissue and the sensor is such that $t1 < \lambda/100$.

11. The device of claim 1, wherein an average distance t1, between external-most surfaces of the tissue and at least one of the plurality of sensors, is less than 500 Angstroms.

12. The device of claim 1, wherein an average distance t1, between external-most surfaces of the tissue and at least one of the plurality of sensors, is less than 50 Angstroms.

13. The device of claim 1, wherein an average distance t1, between external-most surfaces of the tissue and at least one of the plurality of sensors, is less than 5 Angstroms.

14. The device of claim 1, wherein at least one sensor is an irradiative sensor, selected from the group consisting of an optical sensor, an X-ray sensor, an RF sensor, a MW sensor, an infrared thermography sensor, and an ultrasound sensor.

15. The device of claim 1, wherein the at least one sensor is selected from the group consisting of an MR sensor, an impedance sensor, a temperature sensor, a biosensor, a chemical sensor, a radioactive-emission sensor, a nonirradiative RF sensor, and a mechanical sensor.

16. The device of claim 1, wherein the plurality of sensors include at least two different types of sensors.

17. The device of claim 1, wherein the plurality of sensors include at least two different types of sensors, selected from the group consisting of optical sensors, X-ray sensors, RF sensors, MW sensors, infrared thermography sensors, ultrasound sensors, MR sensors, impedance sensors, temperature sensors, biosensors, chemical sensors, radioactive-emission sensors, mechanical sensors, and nonirradiative RF sensors.

18. The device of claim 1, wherein the plurality of sensors includes at least four sensors, arranged as at least two pairs of sensors, each pair being of identical sensors, and each pair representing a different type of sensor, for providing three-dimensional information by at least two modalities.

19. The device of claim 1, wherein the three-dimensional information includes small-scale computerized tomography.

20. The device of claim 1, wherein the mechanism is suction.

21. The device of claim 1, wherein the mechanism is tweezers-like.

22. The device of claim 1, wherein the mechanism is configured to exert physical pressure on the tissue.

23. A tissue-characterization probe, comprising:
a housing, which defines proximal and distal ends, with respect to a tissue;
an element, at the proximal end of the probe, the element defining a rigid surface of a linear cross-section, configured to make contact with the tissue;
a mechanism, adapted for applying a force to the tissue, the line of force being at an acute angle with the rigid surface, for stretching the tissue against the rigid surface, thus achieving effective contact between the tissue and the rigid surface;
a plurality of sensors, in physical contact with the rigid surface, wherein the element defines a curvature of said rigid surface for obtaining three-dimensional information, and further wherein the plurality of sensors includes at least two sensors, arranged along the curvature of the rigid surface, each defining a viewing angle, the at least two sensors sharing a portion of their viewing angles so as to obtain three-dimensional information; and
at least one signal communication line, for providing communication between a signal analyzer and the plurality of sensors.

24. The tissue-characterization probe of claim 23, wherein the mechanism is suction.

25. The tissue-characterization probe of claim 24, wherein a pump configured to provide the suction is arranged within the housing.

26. The tissue-characterization probe of claim 24, wherein the suction is provided by a channel, arranged within the housing and in communication with an external vacuum source.

27. The tissue-characterization probe of claim 26, wherein the channel is further operative to drain off tissue fluids.

28. The tissue-characterization probe of claim 23, configured for an application, selected from the group consisting of extracorporeal application to a skin, intracorporeal insertion through a body lumen, intracorporeal insertion for a minimally invasive procedure, and application to subcutaneous tissue, during open surgery.

29. A tissue-characterization system, comprising:
a housing, which defines proximal and distal ends, with respect to a tissue;
an element, at the proximal end of the probe, the element defining a rigid surface of a linear cross-section, configured to make contact with a tissue;
a mechanism, adapted for applying a force to the tissue, the line of force being at an acute angle with the rigid surface, for stretching the tissue against the rigid surface, thus achieving effective contact between the tissue and the rigid surface;
a plurality of sensors, in physical contact with the rigid surface, wherein the element defines a curvature of said rigid surface for obtaining three-dimensional information, and further wherein the plurality of sensors includes at least two sensors, arranged along the curvature of the rigid surface, each defining a viewing angle, the at least two sensors sharing a portion of their viewing angles so as to obtain three-dimensional information;
a signal analyzer; and
at least one signal communication line, for providing communication between the signal analyzer and the plurality of sensors.

30. A method of tissue characterization, comprising:
providing a tissue characterization probe, which comprises:
an element, which defines a rigid surface of a linear cross-section, configured to make contact with a tissue;
a plurality of sensors, in physical contact with the rigid surface; and
a mechanism, adapted for applying a force to the tissue, the line of force being at an acute angle with the rigid surface, for stretching the tissue against the rigid surface, thus achieving effective contact between the tissue and the rigid surface, wherein the element defines a curvature of said rigid surface for obtaining three-dimensional information, and further wherein the plurality of sensors includes at least two sensors, arranged along the curvature of the rigid surface, each defining a viewing angle, the at least two sensors sharing a portion of their viewing angles so as to obtain three-dimensional information;
applying a force to the tissue, the line of force being at an acute angle with the rigid surface, for stretching the tissue against the rigid surface, thus achieving effective contact between the tissue and the rigid surface; and
characterizing the tissue with the plurality of sensors.

31. A device, comprising:
an element, which defines a surface with a curvature in a first direction, the curvature being at least greater than that of a circle having a diameter of 8 cm; and
at least two sensors, arranged along the curvature, each defining a viewing angle into a volume, the at least two sensors sharing a portion of their viewing angles so as to obtain three-dimensional information of the volume.

32. The device of claim 31, wherein the curvature is greater than that of a circle having a diameter of 6 cm.

33. The device of claim 31, wherein the curvature is greater than that of a circle having a diameter of 4 cm.

34. The device of claim 31, wherein the curvature is greater than that of a circle having a diameter of 2 cm.

35. The device of claim 31, wherein the curvature is greater than that of a circle having a diameter of 1 cm.

36. The device of claim 31, wherein the curvature is greater than that of a circle having a diameter of 0.8 cm.

37. The device of claim 31, wherein the at least two sensors include at least four sensors, arranged as at least two pairs of sensors, each pair being of identical sensors arranged along the curvature, and each pair representing a different type of sensors, for providing three-dimensional information by at least two modalities.

38. A tissue-characterization probe, comprising:
a housing, which defines proximal and distal ends, with respect to a tissue,
an element, which defines a surface with a curvature in a first direction, the curvature being at least greater than that of a circle having a diameter of 8 cm;
at least two sensors, arranged along the curvature, each defining a viewing angle into a volume, the at least two sensors sharing a portion of their viewing angles so as to obtain three-dimensional information of the volume; and
a signal communication architecture, for providing communication between a signal analyzer and the at least two sensors.

39. The tissue-characterization probe of claim 38, configured for insertion to a body lumen.

40. The tissue-characterization probe of claim 37, configured for insertion intracorporeally, for minimally invasive procedures.

41. The tissue-characterization probe of claim 38, configured for application to subcutaneous tissue, during open surgery.

42. The tissue-characterization probe of claim 38, configured for extracorporeal application, wherein the tissue is a skin.

43. A tissue-characterization system, comprising:
a housing, which defines proximal and distal ends, with respect to a tissue,
an element, which defines a surface with a curvature in a first direction, the curvature being at least greater than that of a circle having a diameter of 8 cm; and
at least two sensors, arranged along the curvature, each defining a viewing angle into a volume, the at least two sensors sharing a portion of their viewing angles so as to obtain three-dimensional information of the volume;
a signal analyzer; and
a signal communication architecture, for providing communication between a signal analyzer and one of the at least two sensors.

44. A method of tissue characterization, for obtaining three-dimensional information of a volumetric region within the tissue, comprising:
providing an element, which defines a surface with a curvature in a first direction, having a diameter which is less than 8 cm; and
arranging at least two sensors on the curvature, each defining a viewing angle into a volumetric region, the at least two sensors sharing a portion of their viewing angles;
performing measurements with the at least two sensors; and
analyzing the measurements to obtain the three-dimensional information of the volume.

45. A method of tissue characterization, comprising:
providing an element, which defines a surface with a curvature in a first direction, the curvature having a diameter which is less than 8 cm;
arranging at least two pairs of sensors along the curvature, each pair being of identical sensors, and each pair representing a different type of sensors, for providing three-dimensional information by at least two modalities;
performing measurements with the at least two pairs of sensors; and
analyzing the measurements to obtain the three-dimensional information of a volume, by the at least two modalities.

* * * * *